(12) United States Patent
Dickinson et al.

(10) Patent No.: US 9,782,201 B2
(45) Date of Patent: *Oct. 10, 2017

(54) METHODS FOR FLUID FLOW THROUGH BODY PASSAGES

(71) Applicant: LimFlow GmbH, Dresden (DE)

(72) Inventors: Robert Julian Dickinson, London (GB); Andrew Robert Pacey, Stevenage (GB); Martin Terry Rothman, Santa Rosa, CA (US)

(73) Assignee: LimFlow GmbH, Dresden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/143,864

(22) Filed: May 2, 2016

(65) Prior Publication Data

US 2016/0242896 A1 Aug. 25, 2016

Related U.S. Application Data

(60) Continuation of application No. 14/718,477, filed on May 21, 2015, now Pat. No. 9,326,792, which is a
(Continued)

(30) Foreign Application Priority Data

Apr. 20, 2006 (GB) .................................. 0607761.4

(51) Int. Cl.
*A61F 2/06* (2013.01)
*A61B 17/34* (2006.01)
(Continued)

(52) U.S. Cl.
CPC ............ *A61B 17/3468* (2013.01); *A61F 2/06* (2013.01); *A61F 2/064* (2013.01); *A61F 2/07* (2013.01);
(Continued)

(58) Field of Classification Search
CPC ... A61F 2/07; A61B 19/5244; A61B 17/3468; A61M 25/007
See application file for complete search history.

(56) References Cited

U.S. PATENT DOCUMENTS 4,249,539 A 2/1981 Vilkomerson et al.
4,560,374 A 12/1985 Hammerslag
(Continued)

FOREIGN PATENT DOCUMENTS

WO  WO 00/09041  2/2000
WO  WO 00/33770  6/2000
(Continued)

OTHER PUBLICATIONS

Alexandrescu et al., "Deep calf veins arterialization for inferior limb preservation in diabetic patients with extended ischaemic wounds, unfit for direct arterial reconstruction: preliminary results according to an angiosome model of perfusion", *Cardiovasc. Revasc. Med.*, Jan.-Feb. 2011, vol. 12, pp. 10-19.
(Continued)

*Primary Examiner* — Jason-Dennis Stewart
(74) *Attorney, Agent, or Firm* — Knobbe Martens Olson & Bear, LLP

(57) ABSTRACT

A device includes a first end portion, a second end portion, an intermediate portion between the first end portion and the second end portion, and a graft material coupled to at least the intermediate portion. The first end portion has a first end diameter. The second end portion has a second end diameter larger than the first end diameter. The intermediate portion tapers between the first end portion and the second end portion. A method of diverting fluid flow from a first passage to a second passage comprising deploying the device in a third passage between the first passage and the second passage, expanding the first end portion against sidewalls of
(Continued)

the first passage, and expanding the second end portion against sidewalls of the second passage.

20 Claims, 6 Drawing Sheets

Related U.S. Application Data continuation of application No. 14/592,163, filed on Jan. 8, 2015, now Pat. No. 9,108,018, which is a division of application No. 13/791,185, filed on Mar. 8, 2013, now abandoned, which is a continuation-in-part of application No. 12/297,498, filed as application No. PCT/GB2007/001430 on Apr. 20, 2007, now Pat. No. 8,439,963.

(51) Int. Cl.
    *A61M 27/00*     (2006.01)
    *A61F 2/07*     (2013.01)
    *A61M 1/36*     (2006.01)

(52) U.S. Cl.
    CPC ..... *A61M 27/002* (2013.01); *A61F 2002/072* (2013.01); *A61F 2230/0067* (2013.01); *A61F 2250/001* (2013.01); *A61F 2250/0017* (2013.01); *A61F 2250/0029* (2013.01); *A61F 2250/0031* (2013.01); *A61F 2250/0039* (2013.01); *A61M 1/3655* (2013.01)

(56) References Cited

U.S. PATENT DOCUMENTS

| | | | |
|---|---|---|---|
| 4,739,760 A | 4/1988 | Chin et al. |
| 4,757,821 A | 7/1988 | Snyder |
| 4,952,215 A | 8/1990 | Ouriel et al. |
| 5,047,041 A | 9/1991 | Samuels |
| 5,284,478 A | 2/1994 | Nobles et al. |
| 5,304,189 A | 4/1994 | Goldberg et al. |
| 5,591,226 A | 1/1997 | Trerotola et al. |
| 5,639,278 A | 6/1997 | Dereume et al. |
| 5,720,776 A | 2/1998 | Chuter et al. |
| 5,759,174 A | 6/1998 | Fischell et al. |
| 5,800,522 A | 9/1998 | Campbell et al. |
| 5,897,495 A | 4/1999 | Aida et al. |
| 5,951,599 A | 9/1999 | McCrory |
| 6,165,185 A | 12/2000 | Shennib et al. |
| 6,190,353 B1 | 2/2001 | Makower et al. |
| 6,190,379 B1 | 2/2001 | Heuser et al. |
| 6,193,745 B1 | 2/2001 | Fogarty et al. |
| 6,287,336 B1 | 9/2001 | Globerman et al. |
| 6,302,875 B1 | 10/2001 | Makower et al. |
| 6,364,900 B1 | 4/2002 | Heuser |
| 6,464,665 B1 | 10/2002 | Heuser |
| 6,464,681 B1 | 10/2002 | Heuser |
| 6,475,170 B1 | 11/2002 | Doron et al. |
| 6,475,226 B1 | 11/2002 | Belef et al. |
| 6,536,949 B1 | 3/2003 | Heuser |
| 6,554,842 B2 | 4/2003 | Heuser et al. |
| 6,569,193 B1 | 5/2003 | Cox et al. |
| 6,685,671 B1 | 2/2004 | Oishi et al. |
| 6,726,677 B1 | 4/2004 | Flaherty et al. |
| 6,858,038 B2 | 2/2005 | Heuser |
| 6,863,684 B2 | 3/2005 | Kim et al. |
| 7,018,401 B1 | 3/2006 | Hyodoh et al. |
| 7,166,088 B2 | 1/2007 | Heuser |
| 7,179,250 B2 | 2/2007 | Heuser |
| 7,195,637 B2 | 3/2007 | Mika |
| 7,300,459 B2 | 11/2007 | Heuser |
| 7,402,141 B2 | 7/2008 | Heuser |
| 7,582,108 B2 | 9/2009 | Hierlemann et al. |
| 7,621,902 B2 | 11/2009 | Nita et al. |
| 7,628,768 B2 | 12/2009 | Faul et al. |
| 7,670,329 B2 | 3/2010 | Flaherty et al. |
| 7,780,719 B2 | 8/2010 | Killion et al. |
| 7,849,860 B2 | 12/2010 | Makower et al. |
| 7,914,492 B2 | 3/2011 | Heuser |
| 7,966,057 B2 | 6/2011 | Macaulay et al. |
| 7,967,769 B2 | 6/2011 | Faul et al. |
| 8,048,016 B2 | 11/2011 | Faul et al. |
| 8,066,674 B2 | 11/2011 | Heuser |
| 8,142,387 B2 | 3/2012 | Heise et al. |
| 8,172,861 B2 | 5/2012 | Fuller et al. |
| 8,197,499 B2 | 6/2012 | Gurtner et al. |
| 8,216,259 B2 | 7/2012 | Gurtner et al. |
| 8,226,592 B2 | 7/2012 | Brenneman et al. |
| 8,231,646 B2 | 7/2012 | Kassab et al. |
| 8,251,943 B1 | 8/2012 | Spencer et al. |
| 8,282,591 B2 | 10/2012 | Khan et al. |
| 8,343,087 B2 | 1/2013 | Formichi |
| 8,343,089 B2 | 1/2013 | Chang |
| 8,361,101 B2 | 1/2013 | Kassab |
| 8,414,516 B2 | 4/2013 | Chang |
| 8,439,963 B2 | 5/2013 | Dickinson et al. |
| 8,506,516 B2 | 8/2013 | Kassab et al. |
| 8,540,668 B2 | 9/2013 | Griffin et al. |
| 8,545,418 B2 | 10/2013 | Heuser |
| 8,551,032 B2 | 10/2013 | Faul et al. |
| 8,574,185 B2 | 11/2013 | Faul et al. |
| RE44,639 E | 12/2013 | Squitieri |
| 8,652,084 B2 | 2/2014 | Akingba |
| 8,727,988 B2 | 5/2014 | Flaherty et al. |
| 8,747,344 B2 | 6/2014 | Khan |
| 8,747,345 B2 | 6/2014 | Salloum |
| 8,753,366 B2 | 6/2014 | Makower et al. |
| 8,771,305 B2 | 7/2014 | Shriver |
| 8,784,474 B2 | 7/2014 | Sargent, Jr. |
| 8,808,358 B2 | 8/2014 | Khoury |
| 8,815,278 B2 | 8/2014 | Roorda |
| 8,858,490 B2 | 10/2014 | Chou et al. |
| 8,858,579 B2 | 10/2014 | Suyker et al. |
| 8,870,805 B2 | 10/2014 | Chang |
| 8,888,733 B2 | 11/2014 | Kassab |
| 8,894,681 B2 | 11/2014 | Kassab |
| 8,900,115 B2 | 12/2014 | Bolling et al. |
| 8,905,962 B2 | 12/2014 | Asano et al. |
| 8,915,934 B2 | 12/2014 | Nielsen et al. |
| 8,926,545 B2 | 1/2015 | Brenneman et al. |
| 8,945,039 B2 | 2/2015 | Kassab |
| 8,951,222 B2 | 2/2015 | Tarlian, Jr. et al. |
| 8,968,230 B2 | 3/2015 | Kassab |
| 9,017,323 B2 | 4/2015 | Miller et al. |
| 9,039,702 B2 | 5/2015 | Miller et al. |
| 9,108,018 B2 | 8/2015 | Dickinson et al. |
| 9,259,340 B2 | 2/2016 | Heuser et al. |
| 9,301,830 B2 | 4/2016 | Heuser et al. |
| 9,314,329 B2 | 4/2016 | Dickinson et al. |
| 9,326,792 B2 | 5/2016 | Dickinson et al. |
| 9,486,276 B2 | 11/2016 | Rios et al. |
| 9,532,803 B2 | 1/2017 | Dickenson et al. |
| 9,545,263 B2 | 1/2017 | Lenihan et al. |
| 2001/0041930 A1 | 11/2001 | Globerman et al. |
| 2002/0048310 A1 | 4/2002 | Heuser |
| 2002/0052644 A1 | 5/2002 | Shaolian et al. |
| 2002/0068869 A1 | 6/2002 | Brisken et al. |
| 2002/0089262 A1 | 7/2002 | Topa et al. |
| 2002/0173784 A1 | 11/2002 | Sliwa, Jr. et al. |
| 2003/0125799 A1 | 7/2003 | Limon |
| 2003/0139802 A1 | 7/2003 | Wulfman et al. |
| 2003/0153969 A1 | 8/2003 | Dehdashtian et al. |
| 2004/0122508 A1 | 6/2004 | White et al. |
| 2004/0148005 A1 | 7/2004 | Heuser |
| 2004/0199243 A1 | 10/2004 | Yodfat |
| 2004/0249335 A1 | 12/2004 | Faul et al. |
| 2005/0004648 A1 | 1/2005 | Boekstegers |
| 2005/0165469 A1 | 7/2005 | Hogendijk |
| 2005/0192606 A1 | 9/2005 | Paul, Jr. |
| 2006/0111770 A1 | 5/2006 | Pavcnik et al. |
| 2006/0122554 A1 | 6/2006 | Wilk |
| 2006/0287709 A1 | 12/2006 | Rao |
| 2007/0179590 A1 | 8/2007 | Lu et al. |
| 2007/0185513 A1 | 8/2007 | Woolfson et al. |

(56) References Cited

U.S. PATENT DOCUMENTS

| | | |
|---|---|---|
| 2007/0203515 A1 | 8/2007 | Heuser et al. |
| 2007/0265563 A1 | 11/2007 | Heuser |
| 2008/0009936 A1 | 1/2008 | Kim et al. |
| 2008/0154153 A1 | 6/2008 | Heuser |
| 2008/0161901 A1 | 7/2008 | Heuser et al. |
| 2008/0161904 A1 | 7/2008 | Heuser et al. |
| 2008/0177249 A1 | 7/2008 | Heuser et al. |
| 2008/0194939 A1 | 8/2008 | Dickinson et al. |
| 2008/0228209 A1 | 9/2008 | Demello et al. |
| 2008/0234813 A1 | 9/2008 | Heuser |
| 2009/0012429 A1 | 1/2009 | Heuser |
| 2009/0093791 A1 | 4/2009 | Heuser |
| 2009/0192485 A1 | 7/2009 | Heuser |
| 2010/0082058 A1 | 4/2010 | Kassab |
| 2010/0094391 A1 | 4/2010 | Heraty et al. |
| 2010/0131000 A1 | 5/2010 | Demello et al. |
| 2010/0241214 A1 | 9/2010 | Holzer et al. |
| 2011/0054589 A1 | 3/2011 | Bashiri et al. |
| 2011/0077680 A1 | 3/2011 | Heuser |
| 2011/0197900 A1 | 8/2011 | Heuser |
| 2011/0208109 A1 | 8/2011 | Kassab |
| 2011/0251671 A1 | 10/2011 | Heraty et al. |
| 2011/0264104 A1 | 10/2011 | Naoum |
| 2011/0319902 A1 | 12/2011 | Epstein |
| 2012/0010556 A1 | 1/2012 | Faul et al. |
| 2012/0046678 A1 | 2/2012 | Lemaitre et al. |
| 2012/0046730 A1 | 2/2012 | von Oepen et al. |
| 2012/0095500 A1 | 4/2012 | Heuser |
| 2012/0116354 A1 | 5/2012 | Heuser |
| 2012/0123512 A1 | 5/2012 | Asfora et al. |
| 2012/0150092 A1 | 6/2012 | McAllister et al. |
| 2012/0179238 A1 | 7/2012 | Sarac et al. |
| 2012/0203329 A1 | 8/2012 | Heuser |
| 2012/0239137 A1 | 9/2012 | Heuser et al. |
| 2012/0271400 A1 | 10/2012 | Lyons et al. |
| 2012/0277774 A1 | 11/2012 | Guo |
| 2012/0296368 A1 | 11/2012 | Kassab et al. |
| 2012/0310319 A1 | 12/2012 | Tieu et al. |
| 2013/0023813 A1 | 1/2013 | Roorda |
| 2013/0030461 A1 | 1/2013 | Marks et al. |
| 2013/0041305 A1 | 2/2013 | Tarlian, Jr. et al. |
| 2013/0041306 A1 | 2/2013 | Faul et al. |
| 2013/0053732 A1 | 2/2013 | Heuser |
| 2013/0060323 A1 | 3/2013 | McHugo |
| 2013/0103137 A1 | 4/2013 | Asano et al. |
| 2013/0138139 A1 | 5/2013 | Stanley |
| 2013/0144373 A1 | 6/2013 | Shahriari |
| 2013/0190676 A1 | 7/2013 | Dickinson et al. |
| 2013/0197621 A1 | 8/2013 | Ryan et al. |
| 2013/0204176 A1 | 8/2013 | Duffy et al. |
| 2013/0226067 A1 | 8/2013 | Ward et al. |
| 2013/0226285 A1 | 8/2013 | Strommer |
| 2013/0261531 A1 | 10/2013 | Gallagher et al. |
| 2013/0324901 A1 | 12/2013 | Pillai |
| 2013/0331762 A1 | 12/2013 | Kassab et al. |
| 2014/0039538 A1 | 2/2014 | Kassab et al. |
| 2014/0052170 A1 | 2/2014 | Heuser et al. |
| 2014/0088623 A1 | 3/2014 | Yevzlin et al. |
| 2014/0088681 A1 | 3/2014 | Iyer et al. |
| 2014/0088685 A1 | 3/2014 | Yevzlin et al. |
| 2014/0100508 A1 | 4/2014 | Khan |
| 2014/0100510 A1 | 4/2014 | Yevzlin et al. |
| 2014/0142677 A1 | 5/2014 | Heuser et al. |
| 2014/0142679 A1 | 5/2014 | Motaganahalli |
| 2014/0148751 A1 | 5/2014 | Kassab et al. |
| 2014/0194910 A1 | 7/2014 | Orion et al. |
| 2014/0236274 A1 | 8/2014 | Dickinson et al. |
| 2014/0276335 A1 | 9/2014 | Pate |
| 2014/0324155 A1 | 10/2014 | Paul |
| 2014/0330194 A1 | 11/2014 | Roorda |
| 2014/0343582 A1 | 11/2014 | Asfora et al. |
| 2014/0358064 A1 | 12/2014 | Dorn |
| 2014/0364882 A1 | 12/2014 | Tulleken et al. |
| 2014/0371653 A1 | 12/2014 | Criado et al. |
| 2015/0005872 A1 | 1/2015 | Theobald et al. |
| 2015/0011925 A1 | 1/2015 | Buckman, Jr. et al. |
| 2015/0025616 A1 | 1/2015 | Chang |
| 2015/0032095 A1 | 1/2015 | Heuser |
| 2015/0045728 A1 | 2/2015 | Heuser |
| 2015/0133845 A1 | 5/2015 | Dickinson et al. |
| 2015/0223817 A1 | 8/2015 | Paris et al. |
| 2015/0258308 A1 | 9/2015 | Pate |
| 2015/0313668 A1 | 11/2015 | Miller et al. |
| 2015/0366580 A1 | 12/2015 | Lenihan et al. |
| 2016/0058956 A1 | 3/2016 | Cohn et al. |
| 2016/0096008 A1 | 4/2016 | Park et al. |
| 2016/0128855 A1 | 5/2016 | Heuser et al. |
| 2016/0151066 A1 | 6/2016 | Paris et al. |
| 2016/0166754 A1 | 6/2016 | Kassab et al. |
| 2016/0175087 A1 | 6/2016 | Heuser et al. |
| 2016/0175569 A1 | 6/2016 | Heuser |
| 2016/0199626 A1 | 7/2016 | Paris et al. |
| 2016/0206317 A1 | 7/2016 | Dickinson et al. |

FOREIGN PATENT DOCUMENTS

| | | |
|---|---|---|
| WO | WO 00/45886 | 8/2000 |
| WO | WO 2005/065579 | 7/2005 |
| WO | WO 2014/137830 | 9/2014 |
| WO | WO 2014/145021 | 9/2014 |
| WO | WO 2014/162067 | 10/2014 |
| WO | WO 2014/176458 | 10/2014 |
| WO | WO 2015/017714 | 2/2015 |

OTHER PUBLICATIONS

Busato et al., "The great saphenous vein in situ for the arterialization of the venous arch of the foot", *J. Casc. Bras.*, 2010, vol. 9, No. 3, pp. 119-123.

Djoric et al., "Distal Venous Arterialization and Reperfusion Injury: Focus on Oxidative Status", *Eur. Surg. Res.*, 2012, vol. 48, pp. 200-207.

Djoric, "Early individual experience with distal venous arterialization as a lower limb salvage procedure", *Am. Surg.*, Jun. 2011, vol. 77, No. 6, pp. 726-730 (Abstract Only).

Engelke et al., "Distal Venous Arterialization for Lower Limb Salvage: Angiographic Appearances and Interventional Procedures", *Radiographics*, Sep.-Oct. 2001, vol. 21, No. 5, pp. 1239-1248.

Gasparis et al., "Distal venous arterialization for limb salvage—a case report", *Vasc. Endovascular Surg.*, Nov.-Dec. 2002, vol. 36, No. 6, pp. 469-472 (Abstract Only).

Gavrilenko et al., "Long-term results of venous blood flow arterialization of the leg and foot in patients with critical lower limb ischemia", *Angiol. Sosud. Khir.*, 2007, vol. 13, No. 2, pp. 95-103 (Abstract Only).

Houlind et al., "Early results from an angiosome-directed open surgical technique for venous arterialization in patients with critical limb ischemia", *Diabet. Foot Ankle*, Dec. 2013, vol. 17, No. 4.

Jacob et al., "Vascular surgical society of great britain and ireland: distal venous arterialization for non-reconstructable arterial disease", *Br. J. Surg.*, May 1999, vol. 86, No. 5, p. 694 (Abstract Only).

Kassab et al., "Coronary venous retroperfusion: an old concept, a new approach", *J. Appl. Physiol.*, Feb. 2008, vol. 104, pp. 1266-1272.

Keshelava et al., "Foot venous system arterialization for salvage of nonreconstructable acute ischemic limb: a case report", *J. Vasc. Nurs.*, Mar. 2009, vol. 27, No. 1, pp. 13-16 (Abstract Only).

Kopelman et al., "Prevention of limb loss in critical ischaemia by arterialization of the superficial venous system: an experimental study in dogs", *Cardiovasc. Surg.*, Aug. 1998, vol. 6, No. 4, pp. 384-388 (Abstract Only).

Lengua et al., "Arterialization of the distal veins of the foot for limb salvage in arteritis—Techniques and results", *Ann. Chir.*, Sep. 2001, vol. 126, No. 7, pp. 629-638 (Abstract Only).

Lu et al., "Meta-analysis of the Clinical Effectiveness of Venous Arterialization for Salvage of Critically Ischaemic Limbs", *Eur. J. Vasc. Endovasc. Surg.*, May 2006, vol. 31, pp. 493-499.

(56) References Cited

OTHER PUBLICATIONS

Matarrese et al., "Revascularization of the ischemic hand with arterialization of the venous system", *J. Hand. Surg. Am.*, Dec. 2011, vol. 36, No. 12, pp. 2047-2051 (Abstract Only).

Miasnik et al., "Scintigraphic evaluation of the efficacy of nonstandard methods of treating critical ischemia of the lower limbs", *Khirurgiia (Mosk)*, 2002, vol. 6, pp. 48-51 (Abstract Only).

Mutirangura et al., "Pedal bypass with deep venous arterialization: the therapeutic option in critical limb ischemia and unreconstructable distal arteries", *Vascular*, Dec. 2011, vol. 19, No. 6, pp. 313-319.

Nguyen et al., "Treatment of hand ischemia with arterialization of the venous system of the hand: report of three cases", *Ann. Chir. Plast. Esthet.*, Jun. 2011, vol. 56, No. 3, pp. 200-206 (Abstract Only).

Pederson, "Revascularization of the chronically ischemic hand", *Hand Clin*, Nov. 1999, vol. 15, No. 4, pp. 629-642 (Abstract Only).

Pokrovsky et al., "Arterialization of the hand venous system in patients with critical ischemia and thrombangiitis obliterans", *Angiol. Sosud. Khir.*, 2007, vol. 13, No. 2, pp. 105-111 (Abstract Only).

Rowe et al., "Initial experience with dorsal venous arch arterialization for limb salvage", *Ann. Vasc. Surg.*, Feb.-Mar. 2002, vol. 16, No. 2, pp. 187-192 (Abstract Only).

Sangiorgi et al, "The Cutaneous Microvascular Architecture of Human Diabetic Toe Studied by Corrosion Casting and Scanning Electron Microscopy Analysis", *Anat. Rec.*, Oct. 2010, vol. 293, pp. 1639-1645.

Sasajima et al., "Combined distal venous arterialization and free flap for patients with extensive tissue loss", *Ann. Vasc. Surg.*, Apr. 2010, vol. 24, No. 3, pp. 373-381 (Abstract Only).

Schreve et al., "Comparative study of venous arterialization and pedal bypass in a patient cohort with critical limb ischemia", *Ann. Vasc. Surg.*, Jul. 2014; vol. 28, No. 5, pp. 1123-1127 (Abstract Only).

Sheil, "Treatment of critical ischaemia of the lower limb by venous arterialization : an interim report", *Br. J. Surg.*, Mar. 1977, vol. 64, No. 3, pp. 197-199 (Abstract Only).

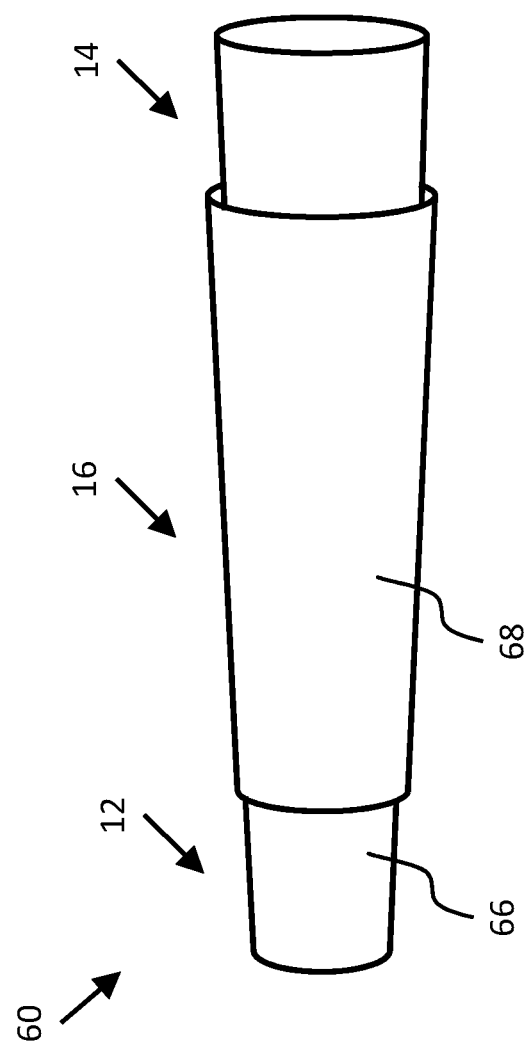

METHODS FOR FLUID FLOW THROUGH BODY PASSAGES

CROSS-REFERENCE TO RELATED APPLICATIONS

This application is a continuation of U.S. patent application Ser. No. 14/718,477, filed May 21, 2015 and issued as U.S. Pat. No. 9,326,792 on May 3, 2016, which is a continuation of U.S. patent application Ser. No. 14/592,163, filed Jan. 8, 2015 and issued as U.S. Pat. No. 9,108,018 on Aug. 18, 2015, which is a divisional of U.S. patent application Ser. No. 13/791,185, filed Mar. 8, 2013, which is a continuation-in-part of U.S. patent application Ser. No. 12/297,498, issued as U.S. Pat. No. 8,439,963 on May 14, 2013 and filed under §371(c) on Feb. 25, 2009 as a U.S. national stage of PCT Patent App. No. PCT/GB2007/001430, filed on Apr. 20, 2007, the contents of which are incorporated herein by reference in their entirety, which claims priority to GB 0607761.4, filed Apr. 20, 2006.

BACKGROUND

The present application relates to devices and methods and for use in percutaneous interventional surgery. In particular, the present application relates to devices and methods for providing or maintaining fluid flow through passages such as heart cavities and blood vessels.

Minimally invasive percutaneous surgery, commonly known as "key-hole" surgery, is a well-known surgical technique wherein surgical devices are inserted into a patient's body through a small aperture cut. For example, it is often preferable to use key-hole surgery in cardiovascular procedures, so as to avoid the substantial discomfort, need for general anesthesia, trauma, high risk of infection, and long recovery time typically associated with conventional surgery.

Key-hole surgery is often used in the treatment of coronary heart disease, in which a coronary artery is partially occluded by a blockage such as an atheroma. For example, in balloon angioplasty, a balloon catheter including a flexible, hollow tube is inserted into an artery, usually near the patient's groin, and is guided through the body to the patient's heart. The heart and the cardiac arteries may be visualised using X-ray fluoroscopy, and the tip of the catheter may be fluorescent so that its position can be determined. The catheter carries an inflatable balloon near its distal tip. The balloon is positioned in or near to the blockage, and then the balloon is inflated so as to widen or dilate the occluded blood vessel to restore blood flow through the coronary artery to the cardiac tissue.

A tubular supporting device (e.g., stent) may be deployed at the site of the blockage to prevent future occlusion (restenosis) or collapse of the blood vessel. The stent may, for example, be an expandable metal mesh tube which is carried on the balloon of the balloon catheter. While on the catheter, the tube has a relatively small diameter in comparison to the diameter of the blood vessel. The stent expands when the balloon is inflated, so that the stent pushes against the wall of the blood vessel. The stent is arranged to retain its expanded shape when it reaches its expanded position, for example by plastic deformation or by means of a mechanical locking mechanism, so as to form a resilient scaffold or support in the blood vessel. The support structure (e.g., stent) supports and dilates the wall of the blood vessel to maintain a pathway for blood to flow through the vessel. Self-expanding stents are also available, which are held in a collapsed state by a suitably adapted catheter for transport through the artery and which adopt an expanded state when deployed at the site of the blockage. The catheter may, for example, include a retaining sleeve which retains the stent in a compressed or unexpanded state. Upon removal or withdrawal of the sleeve from the stent, the stent expands to support and dilate the wall of the blood vessel.

In acute cases of coronary heart disease, where a coronary artery is severely or completely occluded, angioplasty may not be suitable. Instead, coronary bypass surgery may be required. Bypass surgery is an open-chest or open-heart procedure, and typically involves grafting a piece of healthy blood vessel onto the coronary artery so as to bypass the blockage and restore blood flow to the coronary tissue. The healthy blood vessel is usually a vein harvested from the patient's leg or arm during the course of the bypass operation. To perform the procedure, the patient's heart must be exposed by opening the chest, separating the breastbone, and cutting the pericardium surrounding the heart, resulting in significant surgical trauma.

Certain patients are unsuitable as candidates for conventional coronary bypass surgery, due low expectation of recovery or high risk from the significant trauma due to surgery, high risk of infection, absence of healthy vessels to use as bypass grafts, significant co-morbidities, and expected long and complicated recovery time associated with open-chest surgery. For example, factors such as diabetes, age, obesity, and smoking may exclude patients who are in need of treatment.

SUMMARY

Certain embodiments described herein can provide fluid flow in passages such as coronary and/or peripheral blood vessels by creating a bypass using minimally invasive surgical techniques.

In some implementations, a method of diverting fluid flow from a first passage to a second passage comprises deploying a device in a third passage between the first passage and the second passage. The device comprises a first end portion, a second portion, an intermediate portion, and a graft material. The first end portion has a first end diameter. The second end portion has a second end diameter larger than the first end diameter. The intermediate portion is between the first end portion and the second end portion. The intermediate portion tapers between the first end portion and the second end portion. The graft material is coupled to at least the intermediate portion. The method further comprises expanding the first end portion against sidewalls of the first passage and expanding the second end portion against sidewalls of the second passage.

The first passage may be an artery and the second passage may be a vein. The first passage may be a coronary artery and the second passage may be a coronary vein. The method may further comprise dilating the third passage. The first passage may be a peripheral artery and the second passage may be a peripheral vein. The method may further comprise dilating the third passage. Dilating the third passage may comprise expanding the intermediate portion. The first passage may be substantially parallel to the second passage. The intermediate portion may be conformable to an "S" shape. Expanding the first end portion and the second end portion may comprise allowing self-expansion of the first end portion and the second end portion. Expanding the first end portion and the second end portion may comprise balloon expanding at least one of the first end portion and the second end portion. Expanding one of the first end portion and the second end portion may comprise allowing self-expansion of the one of the first end portion and the second end portion and expanding the other of the first end portion and the second end portion may comprise balloon expanding the other of the first end portion and the second end portion. The method may further comprise expanding the intermediate portion.

In some implementations, a device comprises a first end portion, a second end portion, an intermediate portion, and a graft material. The first end portion has a first end diameter. The second end portion has a second end diameter smaller than the first end diameter. The intermediate portion is between the first end portion and the second end portion. The intermediate portion tapers between the first end portion and the second end portion. The graft material is coupled to at least the intermediate portion.

At least one of the first end portion and the second end portion may be substantially cylindrical. The first end portion may be substantially cylindrical and the second end portion may be substantially cylindrical. The first end portion may taper between the first end diameter and the intermediate portion or the second end portion may taper between the second end diameter and the intermediate portion. The first end portion may taper between the first end diameter and the intermediate portion and the second end portion may taper between the second end diameter and the intermediate portion. The first end portion may comprise a first type of material, the second end portion may comprise a second type of material, and the intermediate portion may comprise a third type of material. The first type of material may comprise a first cut material, the second type of material may comprise a second cut material, and the third type of material may comprise filaments. The first cut material may comprise a chromium cobalt alloy, the second cut material may comprise nitinol, and the filaments may comprise nitinol. The first type of material may comprise a cut material, the second type of material may comprise the cut material, and the third type of material may comprise filaments. The cut material may comprise nitinol and the filaments may comprise nitinol. At least one of the first end portion, the second end portion, the intermediate portion, and the graft material may comprise a bioabsorbable material. At least some of the graft material may be outside the intermediate portion. At least some of the graft material may be inside the intermediate portion. At least some of the graft material may be embedded within the intermediate portion. The device may be capable of maintaining fluid flow between a first passage in which the first end portion is anchored and a second passage in which the second end portion is anchored. The first passage may be substantially parallel to the second passage. The intermediate portion may be conformable to an "S" shape.

In some implementations, a device comprises a first end portion, a second end portion, an intermediate portion, and a graft material. The first end portion comprises a first material. The second end portion comprises a second material different than the first material. The intermediate portion is between the first end portion and the second end portion. The graft material is coupled to at least the intermediate portion.

The first material may comprise nitinol and the second material may comprise chromium cobalt. The first material may comprise nitinol and the second material may comprise stainless steel. The first end portion may comprise cut struts and the second end portion may comprise filaments. The first end portion may comprise cut struts and the second end portion may comprise cut struts. The first material may comprise an alloy and the first end portion may comprise struts or filaments having a first thickness, and the second material may comprise the alloy and the second end potion may comprise struts or filaments having a second thickness different than the first thickness. The intermediate portion may comprise a third material. The third material may comprise nitinol. The intermediate portion may comprise filaments. The intermediate portion may comprise cut struts. At least one of the first end portion and the second end portion may be substantially cylindrical. At least one of the first end portion, the second end portion, the intermediate portion, and the graft material may comprise a bioabsorbable material. At least some of the graft material may be outside the intermediate portion. At least some of the graft material may be inside the intermediate portion. At least some of the graft material may be embedded within the intermediate portion. The graft material may be coupled to at least one of the first end portion and the second end portion. The device may be capable of maintaining fluid flow between a first passage in which the first end portion is anchored and a second passage in which the second end portion is anchored. The first passage may be substantially parallel to the second passage. The intermediate portion may be conformable to an "S" shape.

In some implementations, a device comprises a support structure and a graft material. The support structure comprises a first end portion, a second end portion, and an intermediate portion between the first end portion and the second end portion. At least one of the first end portion, the second end portion, and the intermediate portion comprise cut struts and at least one of the first end portion, the second end portion, and the intermediate portion comprise filaments. The graft material is coupled to at least the intermediate portion.

The first end portion and the second end portion comprise cut struts and the intermediate portion may comprise filaments. At least some of the graft material may be outside the intermediate portion. At least some of the graft material may be inside the intermediate portion. At least some of the graft material may be embedded within the intermediate portion. The graft material may be coupled to at least one of the first end portion and the second end portion. The device may be capable of maintaining fluid flow between a first passage in which the first end portion is anchored and a second passage in which the second end portion is anchored. The first passage may be substantially parallel to the second passage. The intermediate portion may be conformable to an "S" shape.

The device may have a diameter between about 1 mm and about 12 mm (e.g., between 2 mm and 6 mm). The device may have a diameter between about 1 mm and about 10 mm (e.g., between 4 mm and 8 mm). The device may have a diameter between about 6 mm and about 25 mm (e.g., between 12 mm and 15 mm). The device may have a diameter between about 20 mm and about 50 mm (e.g., between 35 mm and 40 mm). The device may have a length between about 25 mm and about 150 mm (e.g., between 70 mm and 110 mm). The device may include filaments having a diameter between about 0.001 inches and about 0.01 inches (e.g., between 0.003 inches and 0.006 inches). The device may include struts having a diameter between about 0.001 inches and about 0.01 inches (e.g., between 0.003 inches and 0.006 inches).

In some embodiments, a device for providing or maintaining fluid flow through at least one passage in a human or animal body includes two end portions for anchoring the device in position and an intermediate portion that allows movement of the end portions relative to each another. The end portions and the intermediate portion together define a pathway for fluid flow through the device.

By allowing the two end portions to move relative to each other, the device can respond to movement of the passage or passages in which the device is used. The intermediate portion may be flexible to allow relative movement of the end portions. In some embodiments, the device has varying or differential flexibility along the length of the device or along a length of a portion of the device. Device flexibility can reduce the likelihood of device failure due to fatigue, for example because the magnitude of stresses within the intermediate portion may be relatively low in comparison to stresses on a support structure (e.g., stent) with uniform flexibility along its entire length.

The device may be configured to provide or maintain fluid flow through a single passageway, for example an occluded blood vessel. The intermediate portion may be capable of maintaining fluid flow between proximal and distal portions of the occluded blood vessel. The intermediate portion can pass through a further passage, for example outside the blood vessel, extending between the proximal and distal portions of the blood vessel. The device may be configured for use as a bypass between proximal and distal portions of a single blood vessel, for example an artery or a vein.

The device may be configured to provide fluid flow from an occluded blood passage to another passage. The passages can be interconnected by the intermediate portion passing through a further passage extending between the two passages. The device may be configured for use as a shunt between two passages, for example between an artery and a vein.

In embodiments in which the end portions can move relative to one another by virtue of the intermediate portion, the device may be suitable for use in applications where the end portions are anchored in separate passages that move relative to one another. A pathway for fluid communication to be maintained through the device irrespective of the relative movement of the end portions, and the likelihood of fatigue failure of the device due to cyclic movement of the end portions may be low in comparison to a support structure (e.g., stent) lacking such an intermediate portion.

One or both of the end portions may be diametrically expandable to anchor the device in position. An expanded end portion may, for example, be expandable to meet with and press against the inner sidewalls of a passage to inhibit or prevent substantial sliding or rotation of the end portion within the passage, and/or to dilate the passage. The intermediate portion may be diametrically expandable, for example to dilate the fluid flow pathway.

The device may be in the form of a tube defining a lumen configured to act as a fluid flow pathway. In some embodiments, the tube may be fluid-tight, so as to confine the fluid flow within the lumen of the tube. The tube may include, but is not limited to, a polymeric material, for example a biocompatible polymer such as polytetrafluoroethylene (PTFE) or polyurethane such as polycarbonate aromatic biodurable thermoplastic polyurethane elastomer (e.g., ChronoFlex C® 80A and 55D medical grade, available from AdvanSource Biomaterials of Wilmington, Mass.).

The device may include a supporting structure that supports the end portions. The supporting structure may support the intermediate portion, in which case the supporting structure may be flexible within the intermediate portion to allow movement of the end portions relative to each other.

When a supporting structure is provided, the supporting structure or a portion thereof may be embedded within a wall of the tube. Alternatively or in addition, the structure or a portion of the structure may be located on the outside of the tube or within the lumen of the tube.

The supporting structure may include at least one mesh. For example, a single mesh may extend along the entire length of the device. In another example, each end of the device includes a mesh, in which case the meshes may stop short of the intermediate portion or may extend into the intermediate portion. When a mesh is present in the intermediate portion, the mesh may have a higher density or smaller window size (e.g., a smaller spacing between filaments and/or struts of the mesh) in the end portions than in the intermediate portion so that the device is relatively more flexible in the intermediate portion than in the end portions. The device may be relatively more flexible in the intermediate portion than in the end portions by way of absence of a mesh, or even when including a mesh with substantially uniform or uniform density or window size (e.g., due to factors other than mesh density or window size), or by including a mesh having a non-uniform density.

At least one mesh may include biocompatible metal wire. For example, the metal wire may be stainless steel. Alternatively, or in addition, at least one mesh may include a shape memory material, for example nitinol and/or chromium cobalt. When a shape memory material is used, at least a portion of the device may be self-expanding.

One or both end portions may include anchoring protuberances or barbs capable of and/or configured to dig into or grasp the inside sidewalls of a passage, for example to prevent or reduce slippage or other movement of the or each end portion relative to the passage.

The two end portions may have different diameters, so that the device can be made to fit securely within a passage having variable diameter, or with one end portion in a first passage and the other end portion in a second passage, when the passages have different diameters. The device can be configured for a particular application and/or for a particular patient.

In some embodiments, a method of diverting fluid flow from a first passage to a second passage (e.g., adjacent to the first passage) includes forming a third passage between the first and second passages, providing a device having two end portions and an intermediate portion, deforming the intermediate portion of the device to permit insertion of the device in the passages, and expanding the end portions against the walls of the first and second passages so as to anchor the device in the passages. The intermediate portion of the device may be flexed to permit insertion of the device in the passages. The two end portions and the intermediate portion may be configured to maintain or provide fluid flow through the device.

One or more end portions of the device may be expanded by a balloon catheter. Alternatively, or in addition, at least one end portion may be self-expanding, in which case the method may include providing the device in a retaining sleeve, and removing the retaining sleeve to enable the at least one end portion to expand.

The method may further include expanding the intermediate portion to dilate the third passage, thereby forming a larger pathway for fluid flow from the first passage to the second passage.

The methods described herein may be used in many surgical procedures, and can be performed by minimally invasive (key-hole) techniques. The methods may be particularly suitable for the treatment of coronary heart disease, for example by providing a shunt or bypass to divert arterial blood from an occluded coronary artery to a coronary vein (e.g., adjacent to the coronary artery) and/or by traversing an occlusion in a coronary artery by exiting the artery proximal to the occlusion, extending through subintimal tissue, external tissue, and/or a portion of a proximate vessel, and reentering the coronary artery distal to the occlusion, for peripheral vascular disease such as critical limb ischemia, for example by providing a shunt or bypass to divert arterial blood from an occluded peripheral artery to a peripheral vein and/or by traversing an occlusion in a peripheral vessel by exiting the vessel proximal to the occlusion, extending through subintimal tissue, external tissue, and/or a portion of a proximate vessel, and reentering the vessel distal to the occlusion, and/or for non-occluded vessels, for example by creating a shunt between a healthy artery and a healthy vein that can be used for dialysis access.

In some embodiments, a method of treating coronary heart disease includes diverting arterial blood from a coronary artery to a coronary vein by the methods described herein. In some embodiments, a method of treating critical limb ischemia includes diverting arterial blood from a peripheral artery to a peripheral vein by the methods described herein.

For purposes of summarizing the invention and the advantages that may be achieved, certain objects and advantages are described herein. Not necessarily all such objects or advantages need to be achieved in accordance with any particular embodiment. In some embodiments, the invention may be embodied or carried out in a manner that can achieve or optimize one advantage or a group of advantages without necessarily achieving other objects or advantages.

All of these embodiments are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments.

BRIEF DESCRIPTION OF THE DRAWINGS

These and other features, aspects, and advantages of the present disclosure are described with reference to the drawings of certain embodiments, which are intended to illustrate certain embodiments and not to limit the invention, in which like reference numerals are used for like features, and in which:

FIG. 6 is a side perspective view of yet still another example embodiment of a device for providing fluid flow.

DETAILED DESCRIPTION

Figure 1:
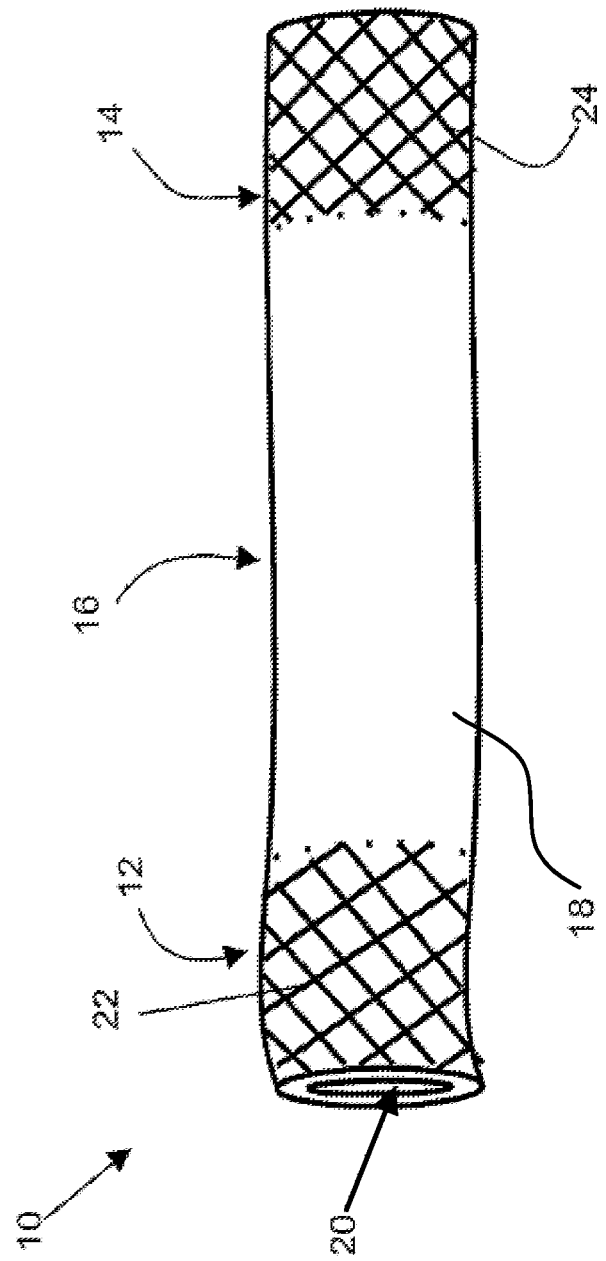
FIG. 1 is a side perspective view of an example embodiment of a device for providing fluid flow.

Although certain embodiments and examples are described below, the invention extends beyond the specifically disclosed embodiments and/or uses and obvious modifications and equivalents thereof. The scope of the invention herein disclosed should not be limited by any particular embodiments described below.

The present application describes devices and methods usable in minimally invasive surgical procedures, which can reduce performance of conventional surgery to treat conditions such as coronary heart disease and critical limb ischemia. For example, patients who might otherwise be unable to receive surgery such as coronary bypass surgery or peripheral arterial bypass surgery can be treated, and the amount of surgical trauma, the risk of infection, and/or the time to recovery may be reduced or significantly reduced in comparison to conventional surgery.

Some methods and devices for performing procedures such as coronary bypass and peripheral arterial bypass by minimally invasive surgical techniques are described in International Patent Application No. PCT/GB05/003480 (Publication No. WO 2006/027599), entitled "Minimally Invasive Surgical Apparatus and Methods," the contents of which are hereby incorporated into this specification by reference in their entirety, in particular techniques for effectively bypassing an occlusion in an artery by percutaneous surgery. These techniques include creating a channel or passage between a first passage, such as an artery upstream of an occlusion, a vein, or a heart chamber, and a second passage, such as an artery, vein, or heart chamber, proximate to the first passage to interconnect the first and second passages by a third passage. Fluid such as blood may be diverted from the first passage into the second passage by way of the interconnecting third passage. In embodiments in which the first passage includes an artery and the second passage includes a vein, the arterial blood can perfuse into tissue in a retrograde manner (retroperfusion).

The interconnecting passage between the first and second passages can be created by, for example, deploying a needle outwards from a first catheter located within the first passage, so that the needle traverses the interstitial tissue or septum between the first and second passages. A second catheter may be located in the second passage, so as to provide a target device which receives a signal, for example an ultrasound signal, transmitted from the first catheter. By monitoring the received signal, the position of the first catheter with respect to the second catheter can be determined so as to ensure that the needle is deployed in the correct position and orientation to create a passage for fluid flow between the first and second passages.

In order to provide or maintain the flow of blood thorough the interconnecting passage or channel, a structure including a lumen may be inserted in the passage to support the interstitial tissue and/or to inhibit or prevent the passage from closing. The tube may, for example, include a stent expanded in the channel using a balloon catheter or self-expansion, as described herein. A catheter to deliver the structure, for example a balloon catheter or catheter that allows self-expansion, may be guided to the channel by a guide wire deployed in the passage by the first catheter.

Passages such as arteries, veins, and heart chambers can pulsate as the heart beats, for example due to movement of heart walls, peripheral limbs, and/or fluctuations in pressure within the passages themselves. This pulsation can cause movement of the passages relative to each another, which can impose stress on a structure within an interconnecting passage therebetween. This stress may be large in comparison to stress experienced by a structure within a single passage. Stress can lead to premature failure of the structure, for example by fatigue failure of the stent struts. Failure of the structure may result in injury to the interstitial tissue and/or occlusion of the interconnecting passage, which could lead to significant complications or complete failure of the therapy.

FIG. 1 illustrates a device or implant or prosthetic 10 for providing or maintaining fluid flow through at least one passage. The device 10 includes a first or proximal end portion 12, a second or distal end portion 14, and an intermediate portion 16 between the proximal end portion 12 and the distal end portion 14. The device includes a bore or lumen 20 for passage of fluid through the device 10. The device 10, for example at least the intermediate portion 16 of the device 10, includes a flexible polymer tube 18. The flexible polymer tube 18 may at least partially define the lumen 20.

The device 10 includes a support structure (e.g., at least one stent) including a mesh 22 and a mesh 24. In some embodiments, at least a portion of the mesh 22 is embedded in the outside wall of the tube 18 proximate to the proximal end portion 12 of the device 10. In some embodiments, at least a portion of the mesh 24, for example a wire or a strut, is embedded in the outside wall of the tube 18 proximate to the distal end portion 14 of the device 10. The meshes 22, 24 may include biocompatible metal such as stainless steel and/or shape memory material such as nitinol or chromium cobalt.

The wire meshes 22, 24 can stiffen the end portions 12, 14, respectively. In some embodiments in which the intermediate portion 16 does not include a mesh, the intermediate portion 16 may be relatively flexible in comparison to the end portions 12, 14, and/or the end portions 12, 14 may have a relatively high radial stiffness.

In some embodiments, the end portions 12, 14 of the device 10 are diametrically expandable. For example, the wire meshes 22, 24 may have a smaller diameter after formation or manufacture than the passages, for example blood vessels, into which the device 10 will be deployed. When the device 10 is in position in the passages, the end portions 12, 14 can be expanded or deformed outwardly so that the respective diameters of the end portions 12, 14 increase, for example to abut the interior sidewalls of the passages. The end portions 12, 14 are configured to maintain the expanded diameter indefinitely, for example by plastic deformation of the material (e.g., wires, struts) of the meshes 22, 24 and/or by provision of a locking mechanism arranged to mechanically lock the meshes 22, 24 in the expanded position. The intermediate portion 16 of the device 10 may be diametrically expandable, for example by way of plastic deformation of the tube 18.

Figure 2:
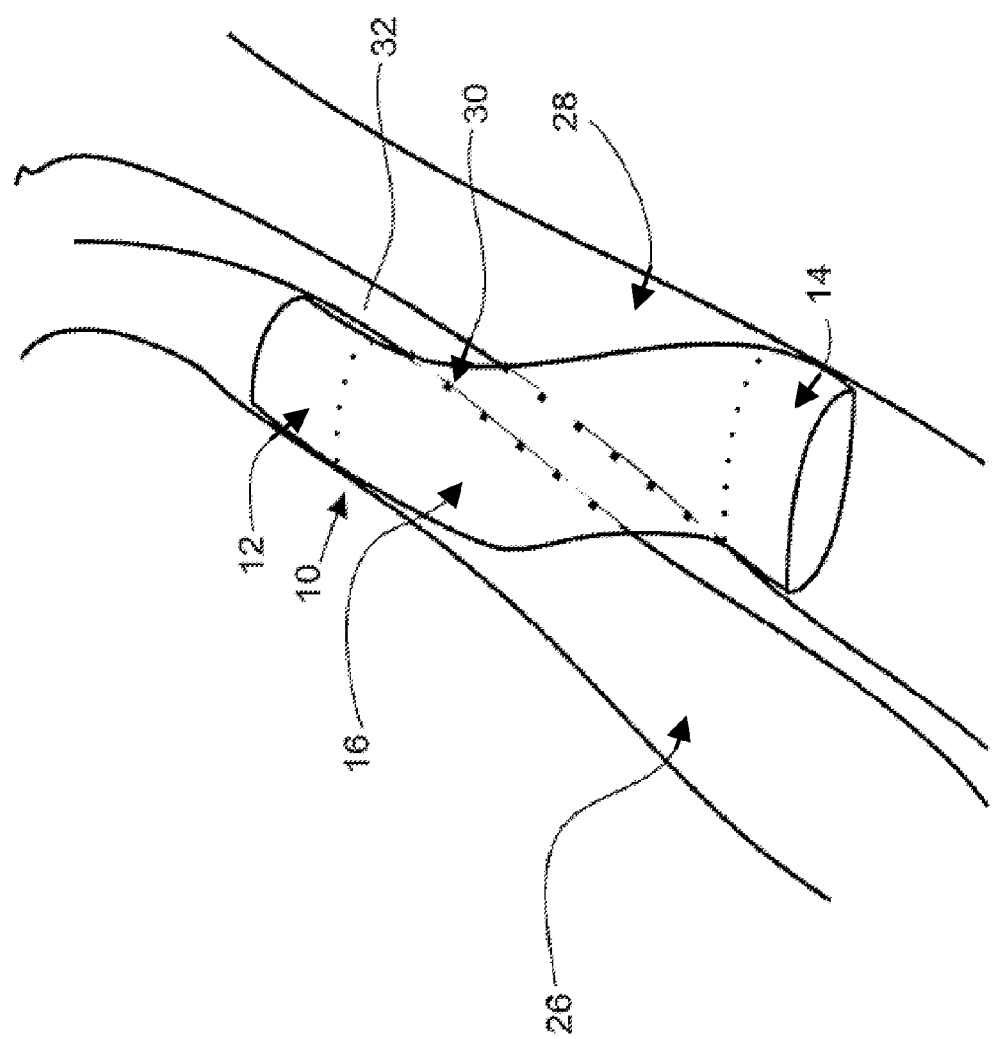
FIG. 2 shows the device of FIG. 1 in use as a shunt between two blood vessels.

FIG. 2 shows the device 10 of FIG. 1 deployed to provide a fluid flow path between a first passage 26 and a second passage 28. The passages 26, 28 may include coronary blood vessels, for example a coronary artery 26 and a coronary vein 28, or vice versa. The passages 26, 28 may include peripheral blood vessels (e.g., blood vessels in limbs), for example a femoral or other peripheral artery 26 and a femoral or other peripheral vein 28, or vice versa. The end portions 12, 14 and the intermediate portion 16 of the device 10 have been expanded to meet with and push against the inner walls of the passages 26, 28. The distal end portion 14 of the device 10 is located within the second passage 28, and the proximal end portion 12 of the device 10 is located within the first passage 26. The intermediate portion 16 extends through an opening or interconnecting passage 30 surgically formed between the passages 26, 28.

The expanded end portions 12, 14 of the device 10 are resilient, and impart an outward radial force on the inner walls of the passages 26, 28. By virtue of the radial stiffness of the end portions 12, 14 of the device 10, the end portions 12, 14 are held or anchored in place within the respective passages 26, 28. Slippage of the device 10 within the passages 26, 28 is thereby prevented or reduced. In this way, the end portions 12, 14 of the device 10 can anchor or fix the device 10 in position, in use, while providing or maintaining fluid flow through the lumen 20 of the tube 18 (FIG. 1). In this way, the device 10 can act as a shunt between the first passage 26 and the second passage 28.

The intermediate portion 16 of the device 10 may be flexible, for example allowing the intermediate portion 16 to form an 'S' shape formed by the combination of the first passage 26, the second passage 28, and the interconnecting passage 30 (FIG. 2). The flexible intermediate portion 16 can allow the end portions 12, 14 of the device 10 to move with respect to one another in response to relative movement of the passages 26, 28.

In embodiments in which the intermediate portion 16 does not include a wire mesh but includes the flexible polymer material of the tube 18, the intermediate portion 16 may not be susceptible to damage due to mesh fatigue, for example upon cyclic or other stress imparted by relative movement of the passages 26, 28.

The intermediate portion 16 of the device 10 has sufficient resilience to maintain dilatation of the interconnecting passage 30, so that the interconnecting passage 30 remains open to provide or maintain a path for blood flow from the artery 26 to the vein 28 by way of the lumen 20 of the tube 18 (FIG. 1). Blood flow from the artery 26 to the vein 28, by way of the interconnecting passage 30, may thereby be provided or maintained through the lumen 20 of the tube 18. The device 10 at least partially supports the artery 26, the vein 28, and the interconnecting passage 30 to provide a pathway for fluid communication through the device 10.

The proximal end portion 12 and the distal end portion 14 of the device 10 are arranged so that, when the device 10 is deployed with the distal end portion 14 in a vein 28 and the proximal end portion 12 in an artery 26, for example as shown in FIG. 2, the diameter of the expanded distal end portion 14 is sufficient to hold the distal end portion 14 within the vein 28, and the diameter of the expanded proximal end portion 12 is sufficient to hold the proximal end portion 12 within the artery 26. The diameter of the proximal end portion 12 may therefore differ from the diameter of the distal end portion 14. By selecting appropriate diameters for the end portions 12, 14 and the intermediate portion 16, the device 10 can be tailored to a certain anatomy and/or the anatomy of an individual patient.

An example procedure for positioning the device 10 of FIG. 1 to provide a shunt between an occluded artery 26 and a vein 28 (e.g., a coronary artery 26 and a coronary vein 28, or a peripheral artery 26 and a peripheral vein 28) to achieve retroperfusion of arterial blood, for example as shown in FIG. 2, will now be described.

A catheter may be inserted into the patient's arterial system by way of a small aperture cut, usually in the patient's groin area. The catheter is fed to the artery 26 and guided to a position upstream of the site of the occlusion, for example at a site proximate and parallel or substantially parallel to a vein 28. A hollow needle is deployed from the catheter, through the wall of the artery 26, through the interstitial tissue 32 that separates the artery 26 and vein 28, and through the wall of the vein 28. The path of the needle creates an interconnecting passage or opening 30, which allows blood to flow between the artery 26 and the vein 28. Deployment of the needle may be guided by a transmitter (e.g., a directional ultrasound transmitter) coupled to a catheter in the artery 26 and a receiver (e.g., an omnidirectional ultrasound receiver) coupled to a catheter in the vein 28, or vice versa, for example as described in International Patent Application No. PCT/GB05/003480. Other methods of forming the opening 30 are also possible (e.g., with or without guidance, from vein to artery, etc.).

Before the needle is withdrawn from the passage 30, a guide wire is inserted through the hollow needle and into the vein 28. The needle is then retracted, leaving the guide wire in place in the artery 26, the passage 30, and the vein 28. The catheter carrying the needle can then be withdrawn from the patient's body. The guide wire can be used to guide further catheters to the interconnecting passage 30 between the artery 26 and the vein 28.

A catheter carrying the device 10 in a non-expanded state is advanced towards the interconnecting passage 30, guided by the guide wire, for example by a rapid exchange lumen or through the lumen 20. The catheter may include, for example, a balloon catheter configured to expand at least a portion of the device 10 and/or a catheter configured to allow self-expansion of at least a portion of the device 10. The distal end portion 14 of the device 10 is passed through the interconnecting passage 30 and into the vein 28, leaving the proximal end portion 12 in the artery 26. The intermediate portion 16 of the device 10 is at least partially in the passage 30, and is at least partially within the artery 26 and the vein 28. The intermediate portion 16 flexes to adopt a curved or "S"-shaped formation, depending on the anatomy of the site. Adoption of such curvature may conform the shape of an intermediate portion 16 extending through the interconnecting passage 30, and optionally into at least one of the passages 26, 28, to the shape of at least the interconnecting passage 30.

The distal end portion 14 of the device 10 is expanded, for example upon inflation of a balloon or by self-expansion, so as to increase the diameter of the distal end portion 14 and anchor the distal end portion 14 against the inner wall of the vein 28. The catheter may be adapted to expand the intermediate portion 16 of the device 10, for example by inflation of a balloon, so that the interconnecting passage 30 can be widened or dilated to obtain blood flow (e.g., sufficient blood flow) from the artery 26 to the vein 28. The proximal end portion 12 of the device 10 is expanded, for example upon inflation of a balloon or by self-expansion, so as to increase the diameter of the proximal end portion 12 and anchor the proximal end portion 12 against the inner wall of the artery 26.

After the end portions 12, 14 of the device 10 are expanded, for example due to self-expansion and/or balloon expansion, and with or without improving expansion after deployment, the catheter and the guide wire are withdrawn from the patient's body. In this way, the device 10 is anchored or fixed in position within the vein 28, the artery 26, and the interconnecting passage 30 as shown in FIG. 2.

The catheter may be adapted to selectively expand the proximal end portion 12, the distal end portion 14, and/or the intermediate portion 16 of the device 10 individually or in combination, for example by the provision of two or more separately inflatable balloons or balloon portions, a single balloon configured to expand all of the portions of the device 10 simultaneously, or a single balloon configured to expand one or more selected portions of the device 10. For example, the end portions 12, 14 may be self-expanding, and the intermediate portion 16 may be expanded by a balloon to dilate the passage 30. In some embodiments including balloon expansion, all or selected parts of the device 10 may be expanded, for example, simultaneously by a balloon across the entire length of the device 10 or by a plurality of balloons longitudinally spaced to selectively inflate selected parts of the device 10, and/or sequentially by a balloon or plurality of balloons. In some embodiments including at least partial self-expansion, all or selected parts of the device 10 may be expanded, for example, by proximal retraction of a sheath over or around the device 10, which can lead to deployment of the device 10 from distal to proximal as the sheath is proximally retracted. Deployment of the device 10 proximal to distal and deployment of the device 10 intermediate first then the ends are also possible.

Other steps may be included in the procedure. For example, before the device 10 is deployed, a balloon catheter may be guided to the interconnecting passage 30 and positioned so that an inflatable balloon portion of the catheter lies in the interconnecting passage 30. Upon inflation of the balloon, the balloon pushes against the walls of the interconnecting passage 30 to widen or dilate the interconnecting passage 30 to ease subsequent insertion of the device 10.

Figure 3:
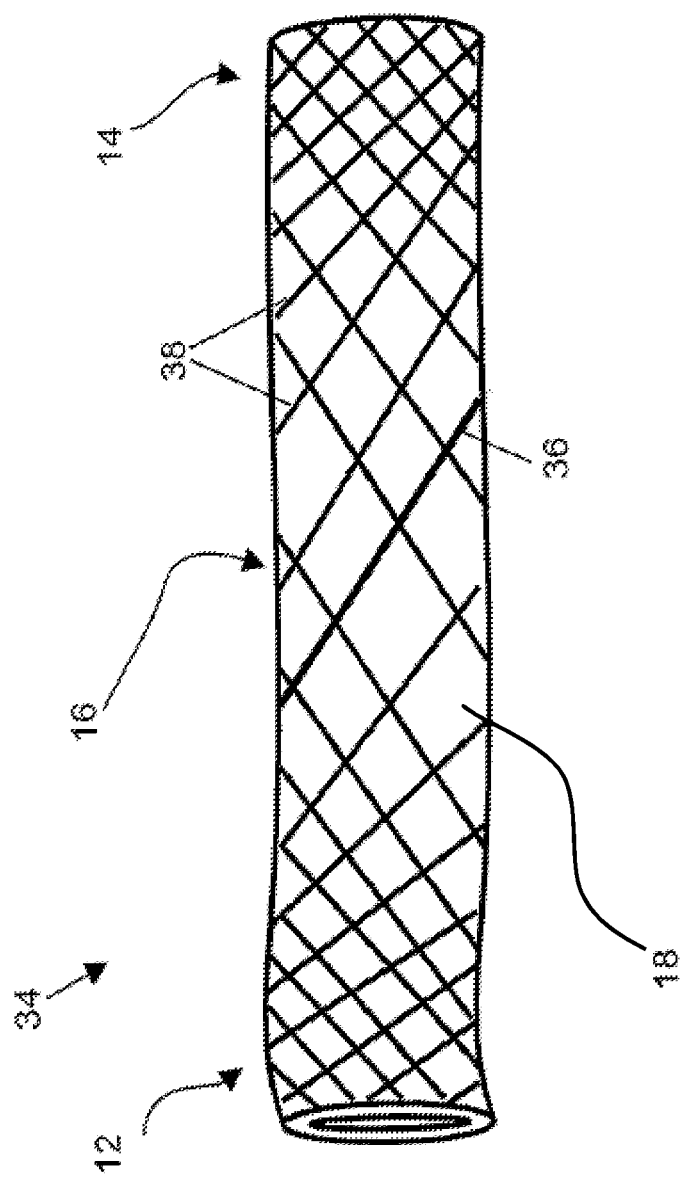
FIG. 3 is a side perspective view of another example embodiment of a device for providing fluid flow.

FIG. 3 illustrates another device 34 for providing fluid flow through at least one passage. The device 34 includes a mesh 36 and a polymer tube 18. The mesh 36 is shown as being on the outside of the polymer tube 18, but as described herein could also or alternatively be on an inside of the polymer tube and/or within the polymer tube 18. As described with respect to the device 10, the device 34 includes a proximal end portion 12, a distal end portion 14, and an intermediate portion 16. In the embodiment illustrated in FIG. 3, the mesh 36 extends along the entire length of the device 34, including along the intermediate portion 16.

In some embodiments, the spacing of filaments or struts of the mesh 36 varies along the length of the device 34. For example, winding density of a woven or layered filamentary mesh may be varied and/or a window size pattern of a cut mesh may be varied.

In some embodiments, the spacing may be relatively small in the proximal end portion 12 and the distal end portions 14, and the spacing may be relatively large in the intermediate portion 16. In other words, the density or window size of the mesh 36 may be relatively low in the intermediate portion 16, and the density or window size of the mesh 36 may be relatively high in the end portions 12, 14. In certain such embodiments, the intermediate portion 16 may be flexible in comparison to the end portions 12, 14. The relatively rigid end portions 12, 14 may engage and anchor in passages. Although the mesh 36 in the intermediate portion 16 may be subject to stress such as cyclic stress, in use, the relatively high flexibility of the intermediate portion 16 due to the low density or window size allows the impact of the stress to be low because the intermediate portion 16 can flex in response to the stress. The risk of fatigue failure of the device 34, and particularly the filaments or struts 38 of the mesh 36, may therefore be reduced in comparison to a device having uniform flexibility along its entire length.

In some embodiments, the spacing may be relatively large in the proximal end portion 12 and the distal end portions 14, and the spacing may be relatively small in the intermediate portion 16. In other words, the density of the mesh 36 may be relatively high (or the window size of the mesh 36 may be relatively low) in the intermediate portion 16, and the density of the mesh 36 may be relatively low (or the window size of the mesh 36 may be relatively high) in the end portions 12, 14. In certain such embodiments, the intermediate portion 16 may have radial strength sufficient to inhibit or prevent collapse of the passage 30, yet still, flexible enough to flex in response to stress such as cyclic stress. The end portions 12, 14 may engage and anchor in passages.

Figure 4:
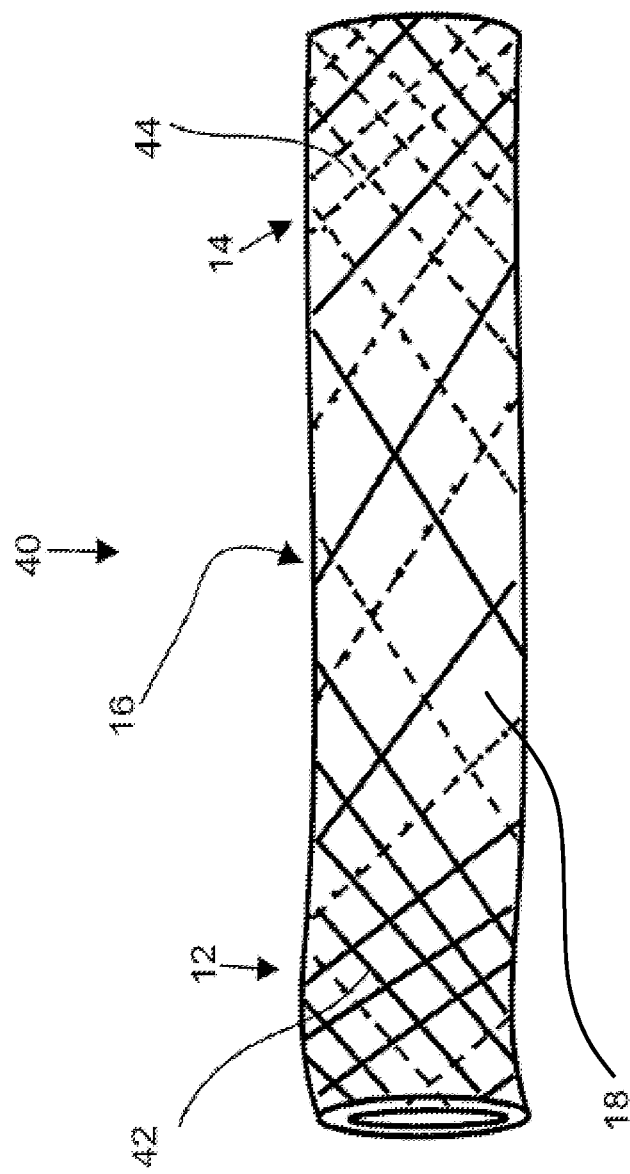
FIG. 4 is a side perspective view of still another example embodiment of a device for providing fluid flow.

FIG. 4 illustrates another device or implant or prosthetic 40 for providing fluid flow through at least one passage. As described with respect to the device 10, the device 40 includes a proximal end portion 12, a distal end portion 14, and an intermediate portion 16. The device 40 includes a polymer tube 18 and a support structure including a first mesh 42 and a second mesh 44. The first mesh 42 extends from the proximal end portion 12 toward (e.g., into) the intermediate portion 16 and optionally into the distal end portion 14. The second mesh 44 extends from the distal end portion 14 toward (e.g., into) the intermediate portion 16 and optionally into the proximal end portion 12. The meshes 42, 44 thereby overlap each other at least in the intermediate portion 16. Both meshes 42, 44 may be on the outside of the tube 18, on the inside of the tube 18, or embedded within the tube 18, or one mesh may be on the outside of the tube 18, on the inside of the tube 18, or embedded within the tube 18 while the other mesh is differently on the outside of the tube 18, on the inside of the tube 18, or embedded within the tube 18 (e.g., one mesh inside the tube 18 and one mesh outside the tube 18). The meshes 42, 44 may be formed, for example, by winding wire in a lattice configuration around or inside the polymer tube 18, by placing a cut tube around or inside the polymer tube 18, by being embedded in the polymer tube 18, combinations thereof, and the like.

In some embodiments, the density of the meshes 42, 44 is relatively high (or the window size of the meshes 42, 44 is relatively low) in their respective end portions 12, 14 and decreases in density (or increases in window size) towards the intermediate portion 16. The total winding density (e.g., the winding density of both meshes 42, 44, taken together) may be lower in the intermediate portion 16 than in the end portions 12, 14, or the total window size (e.g., the window size of both meshes 42, 44, taken together) may be higher in the intermediate portion 16 than in the end portions 12, 14. In certain such embodiments, the intermediate portion 16 is relatively flexible in comparison to the end portions 12, 14. In some embodiments, the meshes 42, 44 do not extend into the intermediate portion, and absence of a mesh could cause the intermediate portion 16 to be relatively flexible in comparison to the end portions 12, 14. In some embodiments, as window size increases (e.g., longitudinally along a tapered portion of the device 40), the density decreases, the mesh coverage decreases, and/or the porosity increases because the width of the struts and/or filaments remains substantially constant or constant or does not increase in the same proportion as the window size, which could provide a change in flexibility along a longitudinal length.

The first and second meshes 42, 44 may include different materials, which can allow optimization of the properties of each of the respective distal and proximal end portions 12, 14 of the device 40 for a particular application of the device 40. For example, the second mesh 44 at the distal end portion 14 of the device 40 may include a relatively flexible metallic alloy for ease of insertion through an interconnecting passage between two blood vessels, while the first mesh 42 at the proximal end portion 12 of the device 40 may include a relatively inelastic metallic alloy to provide a high degree of resilience at the proximal end portion 14 to anchor the device 40 firmly in position. The first and second meshes 42, 44 could include the same material composition (e.g., both including nitinol) but different wire diameters (gauge) or strut thicknesses.

Figure 5:
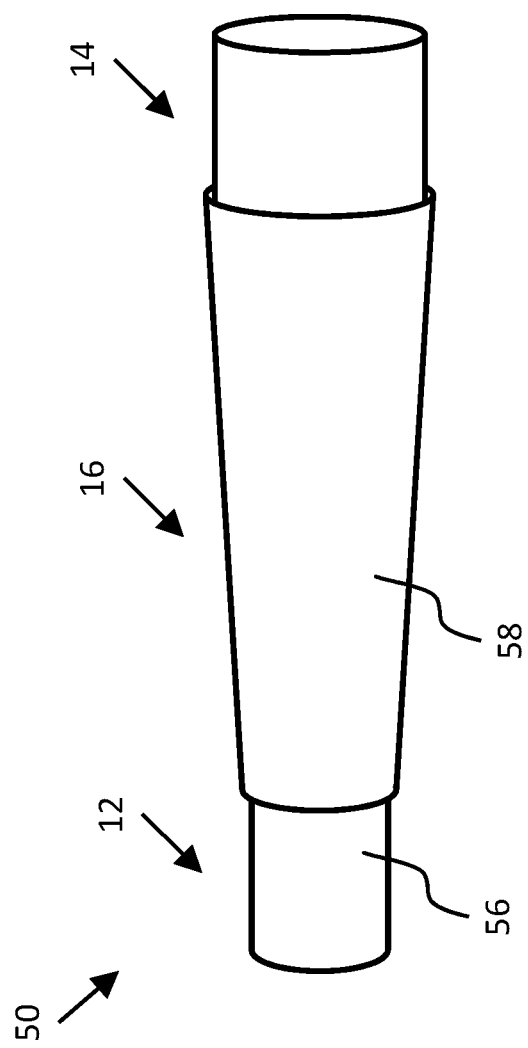
FIG. 5 is a side perspective view of yet another example embodiment of a device for providing fluid flow.

FIG. 5 illustrates another device or implant or prosthetic 50 for providing fluid flow through at least one passage. The device 50 includes a support structure (e.g., stent) 56 and a graft 58. As described with respect to the device 10, the device 50 includes a proximal end portion 12, a distal end portion 14, and an intermediate portion 16. The proximal end portion 12 includes a cylindrical or substantially cylindrical portion and the distal end portion 14 includes a cylindrical or substantially cylindrical portion. The diameter of the proximal end portion 12 is smaller than the diameter of the distal end portion 14. In some embodiments, the diameter of the proximal end portion 12 is larger than the diameter of the distal end portion 14. The intermediate portion 16 has a tapered or frustoconical shape between the proximal end portion 12 and the distal end portion 14. The stent 56 may include filaments (e.g., woven, layered), a cut tube or sheet, and/or combinations thereof.

Parameters of the stent 56 may be uniform or substantially uniform across a portion and/or across multiple portions, or may vary within a portion and/or across multiple portions. For example, the stent 56 at the proximal end portion 12 may include a cut tube or sheet, the stent 56 at the distal end portion 12 may include a cut tube or sheet, and the stent 56 at the intermediate portion 16 may include filaments (e.g., woven or layered). Certain such embodiments may provide good anchoring by the proximal end portion 12 and the distal end portion 14 and good flexibility (e.g., adaptability to third passage sizes and dynamic stresses) of the intermediate portion 16.

The stent 56 may include different materials in different portions. For example, the stent 56 at the proximal end portion 12 may include chromium cobalt and/or tantalum, the stent 56 at the distal end portion 14 may include nitinol, and the stent 56 at the intermediate portion 16 may include nitinol. Certain such embodiments may provide good anchoring and/or wall apposition by the device 50 in each deployment areas (e.g., the proximal end portion 12 engaging sidewalls of an artery, the distal end portion 14 engaging sidewalls of a vein, and the intermediate portion 16 engaging sidewalls of the passage between the artery and the vein).

Combinations of support structure materials and types are also possible. For example, the stent 56 at the proximal portion may include a cut tube or sheet including chromium cobalt and/or tantalum, the stent 56 at the distal end portion 14 may include a cut tube or sheet including nitinol, and the stent 56 at the intermediate portion 16 may include filaments including nitinol.

In embodiments in which the stent 56 includes at least one portion including a cut tube or sheet, the cut pattern may be the same. For example, the cut pattern may be the same in the proximal end portion 12 and the distal end portion 14, but proportional to the change in diameter. In some embodiments, the window size or strut density is uniform or substantially uniform within a portion 12, 14, 16, within two or more of the portions 12, 14, 16, and/or from one end of the stent 56 to the other end of the stent 56. In embodiments in which the stent 56 includes at least one portion including filaments, the winding may be the same. For example, the winding may be the same in the proximal end portion 12 and the distal end portion 14, but changed due to the change in diameter. In some embodiments, the winding density or porosity is uniform or substantially uniform within a portion 12, 14, 16, within two or more of the portions 12, 14, 16, and/or from one end of the stent 56 to the other end of the stent 56. In embodiments in which the stent 56 includes at least one portion including a cut tube or sheet and at least one portion including filaments, the cut pattern and winding may be configured to result in a uniform or substantially uniform density. Non-uniformity is also possible, for example as described herein.

The graft 58 may include materials and attachment to the stent 56 as described with respect to the tube 18. The graft 58 generally forms a fluid-tight passage for at least a portion of the device 50. Although illustrated as only being around the intermediate portion 16, the graft 58 may extend the entire length of the device 50, or may partially overlap into at least one of the cylindrical end portions 12, 14.

FIG. 6 illustrates another device 60 for providing fluid flow through at least one passage. The device 60 includes a support structure (e.g., stent) and a graft 68. As described with respect to the device 10, the device 60 includes a proximal end portion 12, a distal end portion 14, and an intermediate portion 16. The proximal end portion 12 includes a tapered or frustoconical portion and the distal end portion 14 includes a tapered or frustoconical portion. The diameter of the proximal end of the proximal end portion 12 is smaller than the diameter of the distal end of the distal end portion 14. In some embodiments, the diameter of the proximal end of the proximal end portion 12 is larger than the diameter of the distal end of the distal end portion 14. The intermediate portion 16 has a tapered or frustoconical shape between the proximal end portion 12 and the distal end portion 14. In some embodiments, the angle of inclination of the portions 12, 14, 16 is the same or substantially the same (e.g., as illustrated in FIG. 6). In some embodiments, the angle of inclination of at least one portion is sharper or narrower than at least one other portion. The frustoconical proximal end portion 12 and distal end portion 14 may allow better anchoring in a body passage, for example because arteries tend to taper with distance from the heart and veins tend to taper with distance towards the heart, and the end portions 12, 14 can be configured to at least partially correspond to such anatomical taper.

As described above with respect to the support structure 56, the support structure 66 may include filaments (e.g., woven, layered), a cut tube or sheet, the same materials, different materials, and combinations thereof.

The graft 68 may include materials and attachment to the stent 66 as described with respect to the tube 18. The graft 68 generally forms a fluid-tight passage for at least a portion of the device 60. Although illustrated as only being around the intermediate portion 16, the graft 68 may extend the entire length of the device 60, or may partially overlap into at least one of the frustoconical end portions 12, 14.

In some embodiments, a combination of the device 50 and the device 60 are possible. For example, the proximal end portion 12 can be cylindrical or substantially cylindrical (e.g., as in the device 50), the distal end portion 14 can be tapered or frustoconical (e.g., as in the device 60), with the proximal end portion 12 having a larger diameter than the distal end of the distal end portion 14. For another example, the proximal end portion 12 can be tapered or frustoconical (e.g., as in the device 60), the distal end portion 14 can be cylindrical or substantially cylindrical (e.g., as in the device 50), with the proximal end of the proximal end portion 12 having a larger diameter than the distal end portion 14. In each example, the intermediate portion 16 can have a tapered or frustoconical shape between the proximal end portion 12 and the distal end portion 14.

An example deployment device for the implantable devices described herein is described in U.S. patent application Ser. No. 12/545,982, filed Aug. 24, 2009, and U.S. patent application Ser. No. 13/486,249, filed Jun. 1, 2012, the entire contents of each of which is hereby incorporated by reference. The device generally includes a handle at the proximal end with a trigger actuatable by a user and a combination of tubular member at the distal end configured to be pushed and/or pulled upon actuation of the trigger to release the device. Other delivery devices are also possible. The delivery device may include a portion slidable over a guide wire (e.g., a guide wire that has been navigated between the artery and the vein via a tissue traversing needle) and/or may be trackable through a lumen of a catheter.

Although certain embodiments and examples are shown or described herein in detail, various combinations, sub-combinations, modifications, variations, substitutions, and omissions of the specific features and aspects of those embodiments are possible, some of which will now be described by way of example only.

The device, for example a stent of the device, a mesh of the device, a support structure of the device, etc., may be self-expanding. For example, a mesh may include a shape-memory material, such as nitinol, which is capable of returning to a pre-set shape after undergoing deformation. In some embodiments, the stent may be manufactured to a shape that is desired in the expanded configuration, and is compressible to fit inside a sleeve for transport on a catheter to a vascular site. To deploy and expand the stent, the sleeve is drawn back from the stent to allow the shape memory material to return to the pre-set shape, which can anchor the stent in the passages, and which may dilate the passages if the stent has sufficient radial strength. The use of a balloon catheter is not required to expand a fully self-expanding stent, but may be used, for example, to improve or optimize the deployment.

A device may include one or more self-expanding portions, and one or more portions which are expandable by deformation, for example using a balloon catheter. For example, in the embodiment shown in FIG. 4, the first mesh 42 may include stainless steel expandable by a balloon catheter, and the second mesh 44 may include nitinol for self-expansion upon deployment.

With respect to any of the embodiments described herein, the polymer tube 18, including the grafts 58, 68, may include any suitable compliant or flexible polymer, such as PTFE, silicone, polyethylene terephthalate (PET), polyurethane such as polycarbonate aromatic biodurable thermoplastic polyurethane elastomer (e.g., ChronoFlex C® 80A and 55D medical grade, available from AdvanSource Biomaterials of Wilmington, Mass.), combinations thereof, and the like. The polymer tube 18 may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc. The polymer may be in tube form before interaction with a support structure (e.g., stent), or may be formed on, in, and/or around a support structure (e.g., stent). For example, the polymer may include spun fibers, a dip-coating, combinations thereof, and the like. In some embodiments, for example when the device is to be deployed within a single blood vessel, the device may omit the tube. In certain such embodiments, the intermediate portion of the stent may include a mesh with a low winding density or high window size, while the end portions of the stent include a mesh with a higher winding density or lower window size, the mesh being generally tubular to define a pathway for fluid flow through the center of the mesh. In some embodiments, the polymer tube 18 includes a lip (e.g., comprising the same or different material), which can help form a fluid-tight seal between the polymer tube 18 and the body passages. The seal may be angled, for example to account for angled positioning of the polymer tube 18 between body passages. In some embodiments, the polymer tube 18 may extend longitudinally beyond the support structure in at least one direction, and the part extending beyond is not supported by the support structure.

The mesh may include any suitable material, such as nickel, titanium, chromium, cobalt, tantalum, platinum, tungsten, iron, manganese, molybdenum, combinations thereof (e.g., nitinol, chromium cobalt, stainless steel), and the like. The mesh may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc.) and/or glass, and may lack metal. Different materials may be used for portions of the mesh or within the same mesh, for example as previously described with reference to FIG. 4. For example, the mesh 24 at the distal end portion 14 and the mesh 22 at the proximal end portion 12 of the device 10 may include different materials. For another example, the mesh 22, and/or the mesh 24, may include a metallic alloy (e.g., comprising cobalt, chromium, nickel, titanium, combinations thereof, and the like) in combination with a different type of metallic alloy (e.g., a shape memory alloy in combination with a non-shape memory alloy, a first shape memory alloy in combination with a second shape memory alloy different than the first shape memory alloy, a clad material (e.g., comprising a core including a radiopaque material such as titanium, tantalum, rhenium, bismuth, silver, gold, platinum, iridium, tungsten, etc.)) and/or a non-metallic material such as a polymer (e.g., polyester fiber), carbon, and/or bioabsorbable glass fiber. In some embodiments, at least one mesh 22, 24 comprises nitinol and stainless steel. The nitinol may allow some self-expansion (e.g., partial and/or full self-expansion), and the mesh could then be further expanded, for example using a balloon.

Although generally illustrated in FIGS. 1, 3, and 4 as a woven filament mesh, any other structure that can provide the desired degree of resilience may be used. For example, layers of filaments wound in opposite directions may be fused at the filament ends to provide an expandable structure. For another example, a metal sheet may be cut (e.g., laser cut, chemically etched, plasma cut, etc.) to form perforations and then heat set in a tubular formation or a metal tube (e.g., hypotube) may be cut (e.g., laser cut, chemically etched, plasma cut, etc.) to form perforations. A cut tube (including a cut sheet rolled into a tube) may be heat set to impart an expanded configuration.

Filaments or wires or ribbons that may be woven or braided, or layered or otherwise arranged, are generally elongate and have a circular, oval, square, rectangular, etc. transverse cross-section. Example non-woven filaments can include a first layer of filaments wound in a first direction and a second layer of filaments wound in a second direction, at least some of the filament ends being coupled together (e.g., by being coupled to an expandable ring). Example braid patterns include one-over-one-under-one, a one-over-two-under-two, a two-over-two-under-two, and/or combinations thereof, although other braid patterns are also possible. At filament crossings, filaments may be helically wrapped, cross in sliding relation, and/or combinations thereof. Filaments may be loose (e.g., held together by the weave) and/or include welds, coupling elements such as sleeves, and/or combinations thereof. Ends of filaments can be bent back, crimped (e.g., end crimp with a radiopaque material such as titanium, tantalum, rhenium, bismuth, silver, gold, platinum, iridium, tungsten, etc. that can also act as a radiopaque marker), twisted, ball welded, coupled to a ring, combinations thereof, and the like. Weave ends may include filament ends and/or bent-back filaments, and may include open cells, fixed or unfixed filaments, welds, adhesives, or other means of fusion, radiopaque markers, combinations thereof, and the like. Parameters of the filaments may be uniform or substantially uniform across a portion and/or across multiple portions, or may vary within a portion and/or across multiple portions. For example, the proximal end portion 12 may include a first parameter and the distal end portion 14 may include a second parameter different than the first braid pattern. For another example, the proximal end portion 12 and the distal end portion 14 may each include a first parameter and the intermediate portion 16 may include a second parameter different than the parameter. For yet another example, at least one of the proximal end portion 12, the distal end portion 14, and the intermediate portion 16 may include both a first parameter and a second parameter different than the first parameter. Filament parameters may include, for example, filament type, filament thickness, filament material, quantity of filaments, weave pattern, layering, wind direction, pitch, angle, crossing type, filament coupling or lack thereof, filament end treatment, weave end treatment, layering end treatment, quantity of layers, presence or absence of welds, radiopacity, braid pattern, density, porosity, filament angle, braid diameter, winding diameter, and shape setting.

Tubes or sheets may be cut to form strut or cell patterns, struts being the parts of the tube or sheet left after cutting and cells or perforations or windows being the parts cut away. A tube (e.g., hypotube) may be cut directly, or a sheet may be cut and then rolled into a tube. The tube or sheet may be shape set before or after cutting. The tube or sheet may be welded or otherwise coupled to itself, to another tube or sheet, to filaments, to a graft material, etc. Cutting may be by laser, chemical etchant, plasma, combinations thereof, and the like. Example cut patterns include helical spiral, weave-like, coil, individual rings, sequential rings, open cell, closed cell, combinations thereof, and the like. In embodiments including sequential rings, the rings may be coupled using flex connectors, non-flex connectors, and/or combinations thereof. In embodiments including sequential rings, the rings connectors (e.g., flex, non-flex, and/or combinations thereof) may intersect ring peaks, ring valleys, intermediate portions of struts, and/or combinations thereof (e.g., peak-peak, valley-valley, mid-mid, peak-valley, peak-mid, valley-mid, valley-peak, mid-peak, mid-valley). The tube or sheet or sections thereof may be ground and/or polished before or after cutting. Interior ridges may be formed, for example to assist with fluid flow. Parameters of the cut tube or sheet may be uniform or substantially uniform across a portion and/or across multiple portions, or may vary within a portion and/or across multiple portions. For example, the proximal end portion 12 may include a first parameter and the distal end portion 14 may include a second parameter different than the first parameter. For another example, the proximal end portion 12 and the distal end portion 14 may each include a first parameter and the intermediate portion 16 may include a second parameter different than the parameter. For yet another example, at least one of the proximal end portion 12, the distal end portion 14, and the intermediate portion 16 may include both a first parameter and a second parameter different than the first parameter. Cut tube or sheet parameters may include, for example, radial strut thickness, circumferential strut width, strut shape, cell shape, cut pattern, cut type, material, density, porosity, tube diameter, and shape setting.

In some embodiments, the perforations may provide the mesh with a relatively flexible intermediate portion and relatively stiff end portions. The supporting structure may instead be an open-cell foam disposed within the tube.

Filaments of a stent, stent-graft, or a portion thereof, and/or struts of a cut stent, stent-graft, or a portion thereof, may be surface modified, for example to carry medications such as thrombosis modifiers, fluid flow modifiers, antibiotics, etc. Filaments of a stent, stent-graft, or a portion thereof, and/or struts of a cut stent, stent-graft, or a portion thereof, may be at least partially covered with a coating including medications such as thrombosis modifiers, fluid flow modifiers, antibiotics, etc., for example embedded within a polymer layer or a series of polymer layers, which may be the same as or different than the polymer tube 18.

Thickness (e.g., diameter) of filaments of a stent, stent-graft, or a portion thereof, and/or struts of a cut stent, stent-graft, or a portion thereof, may be between about 0.0005 inches and about 0.02 inches, between about 0.0005 inches and about 0.015 inches, between about 0.0005 inches and about 0.01 inches, between about 0.0005 inches and about 0.008 inches, between about 0.0005 inches and about 0.007 inches, between about 0.0005 inches and about 0.006 inches, between about 0.0005 inches and about 0.005 inches, between about 0.0005 inches and about 0.004 inches, between about 0.0005 inches and about 0.003 inches, between about 0.0005 inches and about 0.002 inches, between about 0.0005 inches and about 0.001 inches, between about 0.001 inches and about 0.02 inches, between about 0.001 inches and about 0.015 inches, between about 0.001 inches and about 0.01 inches, between about 0.001 inches and about 0.008 inches, between about 0.001 inches and about 0.007 inches, between about 0.001 inches and about 0.006 inches, between about 0.001 inches and about 0.005 inches, between about 0.001 inches and about 0.004 inches, between about 0.001 inches and about 0.003 inches, between about 0.001 inches and about 0.002 inches, between about 0.002 inches and about 0.02 inches, between about 0.002 inches and about 0.015 inches, between about 0.002 inches and about 0.01 inches, between about 0.002 inches and about 0.008 inches, between about 0.002 inches and about 0.007 inches, between about 0.002 inches and about 0.006 inches, between about 0.002 inches and about 0.005 inches, between about 0.002 inches and about 0.004 inches, between about 0.002 inches and about 0.003 inches, between about 0.003 inches and about 0.02 inches, between about 0.003 inches and about 0.015 inches, between about 0.003 inches and about 0.01 inches, between about 0.003 inches and about 0.008 inches, between about 0.003 inches and about 0.007 inches, between about 0.003 inches and about 0.006 inches, between about 0.003 inches and about 0.005 inches, between about 0.003 inches and about 0.004 inches, between about 0.004 inches and about 0.02 inches, between about 0.004 inches and about 0.015 inches, between about 0.004 inches and about 0.01 inches, between about 0.004 inches and about 0.008 inches, between about 0.004 inches and about 0.007 inches, between about 0.004 inches and about 0.006 inches, between about 0.004 inches and about 0.005 inches, between about 0.005 inches and about 0.02 inches, between about 0.005 inches and about 0.015 inches, between about 0.005 inches and about 0.01 inches, between about 0.005 inches and about 0.008 inches, between about 0.005 inches and about 0.007 inches, between about 0.005 inches and about 0.006 inches, between about 0.006 inches and about 0.02 inches, between about 0.006 inches and about 0.015 inches, between about 0.006 inches and about 0.01 inches, between about 0.006 inches and about 0.008 inches, between about 0.006 inches and about 0.007 inches, between about 0.007 inches and about 0.02 inches, between about 0.007 inches and about 0.015 inches, between about 0.007 inches and about 0.01 inches, between about 0.007 inches and about 0.008 inches, between about 0.008 inches and about 0.02 inches, between about 0.008 inches and about 0.015 inches, between about 0.008 inches and about 0.01 inches, between about 0.01 inches and about 0.02 inches, between about 0.01 inches and about 0.015 inches, or between about 0.015 inches and about 0.02 inches. Other thicknesses are also possible, including thicknesses greater than or less than the identified thicknesses. Filaments and/or struts comprising certain materials (e.g., biodegradable material, materials with less restoring force, etc.) may be thicker than the identified thicknesses.

Thicknesses of filaments and/or struts may be based, for example, on at least one of device or device portion size (e.g., diameter and/or length), porosity, radial strength, material, quantity of filaments and/or struts, cut pattern, weave pattern, layering pattern, and the like. For example, larger filament and/or strut thicknesses (e.g., greater than about 0.006 inches) may be useful for large devices or device portions used to treat large vessels such as coronary vessels, mid-sized filament and/or strut thicknesses (e.g., between about 0.003 inches and about 0.006 inches) may be useful for mid-sized used to treat mid-sized vessels such as peripheral vessels, and small filament and/or strut thicknesses (e.g., less than about 0.003 inches) may be useful for small devices or device portions used to treat small vessels such as veins and neurological vessels.

The internal or external diameter of a stent, a stent-graft, or a first end portion, second end portion, intermediate portion, or subportion thereof, for example taking into account filament or strut thickness, may be between about 1 mm and about 12 mm, between about 1 mm and about 10 mm, between about 1 mm and about 8 mm, between about 1 mm and about 6 mm, between about 1 mm and about 4 mm, between about 1 mm and about 2 mm, between about 2 mm and about 12 mm, between about 2 mm and about 10 mm, between about 2 mm and about 8 mm, between about 2 mm and about 6 mm, between about 2 mm and about 4 mm, between about 4 mm and about 12 mm, between about 4 mm and about 10 mm, between about 4 mm and about 8 mm, between about 4 mm and about 6 mm, between about 6 mm and about 12 mm, between about 6 mm and about 10 mm, between about 6 mm and about 8 mm, between about 8 mm and about 12 mm, between about 8 mm and about 10 mm, or between about 10 mm and about 12 mm. Certain such diameters may be suitable for treating, for example, coronary vessels. The internal or external diameter of a stent, a stent-graft, or a portion thereof, for example taking into account filament or strut thickness, may be between about 1 mm and about 10 mm, between about 1 mm and about 8 mm, between about 1 mm and about 6 mm, between about 1 mm and about 4 mm, between about 1 mm and about 2 mm, between about 2 mm and about 10 mm, between about 2 mm and about 8 mm, between about 2 mm and about 6 mm, between about 2 mm and about 4 mm, between about 4 mm and about 10 mm, between about 4 mm and about 8 mm, between about 4 mm and about 6 mm, between about 6 mm and about 8 mm, or between about 8 mm and about 10 mm. Certain such diameters may be suitable for treating, for example, veins. The internal or external diameter of a stent, a stent-graft, or a portion thereof, for example taking into account filament or strut thickness, may be between about 6 mm and about 25 mm, between about 6 mm and about 20 mm, between about 6 mm and about 15 mm, between about 6 mm and about 12 mm, between about 6 mm and about 9 mm, between about 9 mm and about 25 mm, between about 9 mm and about 20 mm, between about 9 mm and about 15 mm, between about 9 mm and about 12 mm, between about 12 mm and about 25 mm, between about 12 mm and about 20 mm, between about 12 mm and about 15 mm, between about 15 mm and about 25 mm, between about 15 mm and about 20 mm, or between about 20 mm and about 25 mm. Certain such diameters may be suitable for treating, for example, peripheral vessels. The internal or external diameter of a stent, a stent-graft, or a portion thereof, for example taking into account filament or strut thickness, may be between about 20 mm and about 50 mm, between about 20 mm and about 40 mm, between about 20 mm and about 35 mm, between about 20 mm and about 30 mm, between about 30 mm and about 50 mm, between about 30 mm and about 40 mm, between about 30 mm and about 35 mm, between about 35 mm and about 50 mm, between about 35 mm and about 40 mm, or between about 40 mm and about 50 mm. Certain such diameters may be suitable for treating, for example, aortic vessels. Other diameters are also possible, including diameters greater than or less than the identified diameters. The diameter of the device may refer to the diameter of the first end portion, the second end portion, or the intermediate portion, each of which may be in expanded or unexpanded form. The diameter of the device may refer to the average diameter of the device when all of the portions of the device are in either expanded or unexpanded form.

The length of a stent, a stent-graft, or a first end portion, second end portion, intermediate portion, or subportion thereof may be between about 5 mm and about 150 mm, between about 5 mm and about 110 mm, between about 5 mm and about 70 mm, between about 5 mm and about 50 mm, between about 5 mm and about 25 mm, between about 5 mm and about 20 mm, between about 5 mm and about 10 mm, between about 10 mm and about 150 mm, between about 10 mm and about 110 mm, between about 10 mm and about 70 mm, between about 10 mm and about 50 mm, between about 10 mm and about 25 mm, between about 10 mm and about 20 mm, between about 20 mm and about 150 mm, between about 20 mm and about 110 mm, between about 20 mm and about 70 mm, between about 20 mm and about 50 mm, between about 20 mm and about 25 mm, between about 25 mm and about 150 mm, between about 25 mm and about 110 mm, between about 25 mm and about 70 mm, between about 25 mm and about 50 mm, between about 50 mm and about 150 mm, between about 50 mm and about 110 mm, between about 50 mm and about 70 mm, between about 70 mm and about 150 mm, between about 70 mm and about 110 mm, or between about 110 mm and about 150 mm. Other lengths are also possible, including lengths greater than or less than the identified lengths.

The porosity of a stent, a stent-graft, or a first end portion, second end portion, intermediate portion, or subportion thereof may be between about 5% and about 95%, between about 5% and about 50%, between about 5% and about 25%, between about 5% and about 10%, between about 10% and about 50%, between about 10% and about 25%, between about 25% and about 50%, between about 50% and about 95%, between about 50% and about 75%, between about 50% and about 60%, between about 60% and about 95%, between about 75% and about 90%, between about 60% and about 75%, and combinations thereof. The density of a stent may be inverse to the porosity of that stent. The porosity of a portion of a stent covered by a graft may be about 0%. The porosity may vary by objectives for certain portions of the stent. For example, the intermediate portion may have a low porosity to increase fluid flow through the device, while end portions may have lower porosity to increase flexibility and wall apposition.

The radial strength or compression resistance of a stent, a stent-graft, or a first end portion, second end portion, intermediate portion, or subportion thereof may be between about 0.1 N/mm and about 0.5 N/mm, between about 0.2 N/mm and about 0.5 N/mm, between about 0.3 N/mm and about 0.5 N/mm, between about 0.1 N/mm and about 0.3 N/mm, between about 0.1 N/mm and about 0.2 N/mm, between about 0.2 N/mm and about 0.5 N/mm, between about 0.2 N/mm and about 0.3 N/mm, or between about 0.3 N/mm and about 0.5 N/mm.

The values of certain parameters of a stent, a stent-graft, or a first end portion, second end portion, intermediate portion, or subportion thereof may be linked (e.g., proportional). For example, a ratio of a thickness of a strut or filament to a diameter of a device portion comprising that strut or filament may be between about 1:10 and about 1:250, between about 1:25 and about 1:175, or between about 1:50 and about 1:100. For another example, a ratio of a length of a device or portion thereof to a diameter of a device or a portion thereof may be between about 1:1 and about 50:1, between about 5:1 and about 25:1, or between about 10:1 and about 20:1.

Portions of the device may include radiopaque material. For example, filaments and/or struts a stent, a stent-graft, or a first end portion, second end portion, intermediate portion, or subportion thereof may comprise (e.g., be at least partially made from) titanium, tantalum, rhenium, bismuth, silver, gold, platinum, iridium, tungsten, combinations thereof, and the like. For another example, filaments and/or struts of a stent, stent-graft, or a portion thereof may comprise (e.g., be at least partially made from) a material having a density greater than about 9 grams per cubic centimeter. Separate radiopaque markers may be attached to certain parts of the device. For example, radiopaque markers can be added to the proximal end of the device or parts thereof (e.g., a proximal part of the intermediate portion, a proximal part of the distal portion), the distal end of the device or parts thereof (e.g., a distal part of the intermediate portion, a distal part of the proximal portion), and/or other parts. A radiopaque marker between ends of a device may be useful, for example, to demarcate transitions between materials, portions, etc. Radiopacity may vary across the length of the device. For example, the proximal portion could have a first radiopacity (e.g., due to distal portion material and/or separate markers) and the distal portion could have a second radiopacity (e.g., due to distal portion material and/or separate markers) different than the first radiopacity.

In some embodiments, the device includes a polymer tube, and no supporting structure is provided. The intermediate portion of such a device may be relatively more flexible than the end portions by, for example, decreasing the wall thickness of the polymer tube within the intermediate portion.

When a mesh or other supporting structure is provided in combination with a polymer tube, the supporting structure may be located around the outside of the tube, in the inner bore of the tube, or embedded within a wall of the tube. More than one supporting structure may be provided, in which case each supporting structure may have a different location with respect to the tube.

One or both of the end portions of the device may include anchoring elements such as hooks, protuberances, or barbs configured to grasp or grip inner sidewalls of a blood vessel. The radial force of the end portions after expansion may be sufficient to grasp or grip inner sidewalls of a blood vessel without anchoring elements.

There need not be a well-defined transition between the intermediate and end portions. For example, mesh type, material, wall thickness, flexibility, etc. may gradually change from an end portion toward an intermediate portion or from an intermediate portion toward an end portion.

The flexibility of the device may increase gradually when moving from an end portion towards the intermediate portion, for example as described with respect to the devices 34, 40. The change in flexibility may be due to change in mesh density (e.g., winding density, window size), tube thickness, or other factors. The flexibility of the device may be uniform or substantially uniform along the entire length of the support structure (e.g., stent), or along certain portions of the support structure (e.g., along an entire end portion, along the entire intermediate portion, along one end portion and the intermediate portion but not the other end portion, etc.).

While the devices described herein may be particularly suitable for use as a transvascular shunt in percutaneous surgery, the devices could be used in many other medical applications. For example, the devices could be used in angioplasty for the treatment of occluded blood vessels with tortuous or kinked paths, or where the vessels may be subject to deflection or deformation at or near the position of the stent. The stent could also be used for the repair of damaged blood vessels, for example in aortic grafting procedures or after perforation during a percutaneous procedure. In certain such cases, the intermediate portion of the device can allow the device to conform to the shape of the blood vessel and to deform in response to movement of the vessel with reduced risk of fatigue failure while remaining fixed or anchored in position by the end portions. For another example, the devices could be used to form a shunt between a healthy artery and a healthy vein for dialysis access and/or access for administration of medications (e.g., intermittent injection of cancer therapy, which can damage vessels).

While the devices described herein may be used in applications in which the fluid that flows through the device is a liquid such as blood, the devices could be used in applications such as tracheal or bronchial surgery where the fluid is a gas, such as air. In some embodiments, the fluid may contain solid matter, for example emboli or, in gastric surgery where the fluid includes food particles.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

EXAMPLE EMBODIMENTS

The following example embodiments identify some possible permutations of combinations of features disclosed herein, although other permutations of combinations of features are also possible.

1. A method of diverting fluid flow from a first passage to a second passage, the method comprising:
    deploying a device in a third passage between the first passage and the second passage, the device comprising;
        a first end portion having a first end diameter;
        a second end portion having a second end diameter larger than the first end diameter;
        an intermediate portion between the first end portion and the second end portion, the intermediate portion tapering between the first end portion and the second end portion; and
        a graft material coupled to at least the intermediate portion;
    expanding the first end portion against sidewalls of the first passage; and
    expanding the second end portion against sidewalls of the second passage.
2. The method of Embodiment 1, wherein the first passage is an artery and the second passage is a vein.
3. The method of Embodiment 2, wherein the first passage is a coronary artery and the second passage is a coronary vein.
4. The method of Embodiment 2, wherein the first passage is a peripheral artery and the second passage is a peripheral vein.
5. The method of any one of Embodiments 1-4, further comprising dilating the third passage.
6. The method of Embodiment 5, wherein dilating the third passage comprises expanding the intermediate portion.
7. The method of any one of Embodiments 1-6, wherein the first passage is substantially parallel to the second passage.
8. The method of any one of Embodiments 1-7, wherein the intermediate portion is conformable to an "S" shape.
9. The method of any one of Embodiments 1-8, wherein expanding the first end portion and the second end portion comprises allowing self-expansion of the first end portion and the second end portion.
10. The method of any one of Embodiments 1-9, wherein expanding the first end portion and the second end portion comprises balloon expanding at least one of the first end portion and the second end portion.
11. The method of any one of Embodiments 1-10, wherein expanding one of the first end portion and the second end portion comprises allowing self-expansion of the one of the first end portion and the second end portion and wherein expanding the other of the first end portion and the second end portion comprises balloon expanding the other of the first end portion and the second end portion.
12. The method of any one of Embodiments 1-11, further comprising expanding the intermediate portion.
13. A device comprising:
    a first end portion having a first end diameter;
    a second end portion having a second end diameter smaller than the first end diameter;
    an intermediate portion between the first end portion and the second end portion, the intermediate portion tapering between the first end portion and the second end portion; and
    a graft material coupled to at least the intermediate portion.
14. The device of Embodiment 13, wherein at least one of the first end portion and the second end portion is substantially cylindrical.

15. The device of Embodiment 14, wherein the first end portion is substantially cylindrical and the second end portion is substantially cylindrical.
16. The device of any one of Embodiments 13-15, wherein the first end portion tapers between the first end diameter and the intermediate portion, or wherein the second end portion tapers between the second end diameter and the intermediate portion.
17. The device of any one of Embodiments 13-15, wherein the first end portion tapers between the first end diameter and the intermediate portion and the second end portion tapers between the second end diameter and the intermediate portion.
18. The device of any one of Embodiments 13-17, wherein the first end portion comprises a first type of material, the second end portion comprises a second type of material, and the intermediate portion comprises a third type of material.
19. The device of Embodiment 18, wherein the first type of material comprises a first cut material, the second type of material comprises a second cut material, and the third type of material comprises filaments.
20. The device of Embodiment 19, wherein the first cut material comprises a chromium cobalt alloy, the second cut material comprises nitinol, and the filaments comprises nitinol.
21. The device of Embodiment 18, wherein the first type of material comprises a cut material, the second type of material comprises the cut material, and the third type of material comprises filaments.
22. The device of Embodiment 21, wherein the cut material comprises nitinol and the filaments comprises nitinol.
23. The device of any one of Embodiments 13-22, wherein at least one of the first end portion, the second end portion, the intermediate portion, and the graft material comprises a bioabsorbable material.
24. The device of any one of Embodiments 13-23, wherein at least some of the graft material is outside the intermediate portion, at least some of the graft material is inside the intermediate portion, or at least some of the graft material is embedded within the intermediate portion.
25. The device of any one of Embodiments 13-24, wherein the device is capable of maintaining fluid flow between a first passage in which the first end portion is anchored and a second passage in which the second end portion is anchored.
26. The device of Embodiment 25, wherein the first passage is substantially parallel to the second passage.
27. The device of Embodiment 25 or 26, wherein the intermediate portion is conformable to an "S" shape.
28. A device comprising:
a first end portion comprising a first material;
a second end portion comprising a second material different than the first material;
an intermediate portion between the first end portion and the second end portion; and
a graft material coupled to at least the intermediate portion.
29. The device of Embodiment 28, wherein the first material comprises nitinol and the second material comprises chromium cobalt.
30. The device of Embodiment 28 or 29, wherein the first material comprises nitinol and the second material comprises stainless steel.
31. The device of any one of Embodiments 28-30, wherein the first end portion comprises cut struts and the second end portion comprises filaments.
32. The device of any one of Embodiments 28-31, wherein the first end portion comprises cut struts and the second end portion comprises cut struts.
33. The device of any one of Embodiments 28-33, wherein the first material comprises an alloy and the first end portion comprises struts or filaments having a first thickness, and wherein the second material comprises the alloy and the second end potion comprises struts or filaments having a second thickness different than the first thickness.
34. The device of any one of Embodiments 28-33, wherein the intermediate portion comprises a third material.
35. The device of Embodiment 34, wherein the third material comprises nitinol.
36. The device of any one of Embodiments 28-35, wherein the intermediate portion comprises filaments.
37. The device of any one of Embodiments 28-36, wherein the intermediate portion comprises cut struts.
38. The device of any one of Embodiments 28-37, wherein at least one of the first end portion and the second end portion is substantially cylindrical.
39. The device of any one of Embodiments 28-38, wherein at least one of the first end portion, the second end portion, the intermediate portion, and the graft material comprises a bioabsorbable material.
40. The device of any one of Embodiments 28-39, wherein at least some of the graft material is outside the intermediate portion, at least some of the graft material is inside the intermediate portion, or at least some of the graft material is embedded within the intermediate portion.
41. The device of any one of Embodiments 28-41, wherein the graft material is coupled to at least one of the first end portion and the second end portion.
42. The device of any one of Embodiments 28-42, wherein the device is capable of maintaining fluid flow between a first passage in which the first end portion is anchored and a second passage in which the second end portion is anchored.
43. The device of Embodiment 42, wherein the first passage is substantially parallel to the second passage.
44. The device of Embodiment 42 or 43, wherein the intermediate portion is conformable to an "S" shape.
45. A device comprising:
a support structure comprising
a first end portion;
a second end portion;
an intermediate portion between the first end portion and the second end portion, at least one of the first end portion, the second end portion, and the intermediate portion being comprising cut struts and at least one of the first end portion, the second end portion, and the intermediate portion comprising filaments; and
a graft material coupled to at least the intermediate portion.
46. The device of Embodiment 45, wherein the first end portion and the second end portion comprise cut struts and the intermediate portion comprises filaments.
47. The device of Embodiment 45 or 46, wherein at least some of the graft material is outside the intermediate portion, at least some of the graft material is inside the intermediate portion, or at least some of the graft material is embedded within the intermediate portion.

48. The device of any one of Embodiments 45-47, wherein the graft material is coupled to at least one of the first end portion and the second end portion.

49. The device of any one of Embodiments 45-48, wherein the device is capable of maintaining fluid flow between a first passage in which the first end portion is anchored and a second passage in which the second end portion is anchored.

50. The device of Embodiment 49, wherein the first passage is substantially parallel to the second passage.

51. The device of Embodiment 49 or 50, wherein the intermediate portion is conformable to an "S" shape.

What is claimed is:

1. A method of forming a channel between a first vessel and a second vessel, the method comprising:
   forming a passage between the first vessel and the second vessel, wherein the first vessel is an artery and the second vessel is a vein;
   deploying a device in the first vessel, the second vessel, and the passage, the device comprising:
      a longitudinal axis;
      a first end portion having a first radial stiffness, the first end portion having a first length along the longitudinal axis;
      a second end portion having a second radial stiffness, the second end portion having a second length along the longitudinal axis; and
      an intermediate portion between the first end portion and the second end portion, the intermediate portion having a third radial stiffness less than the first radial stiffness and the second radial stiffness, the intermediate portion having a third length along the longitudinal axis;
   wherein deploying the device in the first vessel, the second vessel, and the passage comprises:
      expanding the first end portion against sidewalls of the first vessel;
      expanding the second end portion against sidewalls of the second vessel; and
      expanding the intermediate portion in the passage, wherein expanding the intermediate portion comprises the dilating the passage.

2. The method of claim 1, wherein expanding at least one of the first end portion and the second end portion comprises allowing self-expansion of at least one of the first end portion and the second end portion.

3. The method of claim 1, wherein expanding at least one of the first end portion and the second end portion comprises balloon expanding at least one of the first end portion and the second end portion.

4. The method of claim 1, further comprising a polymer material coupled to at least the intermediate portion, wherein the first end portion has a first diameter, wherein the first end portion is substantially cylindrical, wherein the second end portion has a second diameter larger than the first diameter, and wherein the intermediate portion tapers between the first end portion and the second end portion.

5. The method of claim 1,
   wherein forming the passage comprises:
      inserting a first catheter in the first vessel upstream of an occlusion site in the first vessel; and
      deploying a needle from the first catheter, through tissue between the first vessel and the second vessel, and into the second vessel, and
   wherein deploying the device in the first vessel, the second vessel, and the passage further comprises:
      inserting a guidewire through the needle;
      retracting the needle and the catheter;
      guiding a delivery catheter carrying the device to the passage using the guidewire; and
      deploying the device from the delivery catheter.

6. A method of forming a channel between a first vessel and a second vessel, the method comprising:
   deploying a device in the first vessel, the second vessel, and a passage between the first vessel and the second vessel, the device comprising:
      a longitudinal axis;
      a first end portion having a first radial stiffness;
      a second end portion having a second radial stiffness; and
      an intermediate portion between the first end portion and the second end portion, the intermediate portion having a third radial stiffness less than the first radial stiffness and the second radial stiffness;
   wherein deploying the device in the first vessel, the second vessel, and the passage comprises:
      expanding the first end portion against sidewalls of the first vessel;
      expanding the second end portion against sidewalls of the second vessel; and
      expanding the intermediate portion in the passage, wherein expanding the intermediate portion comprises the dilating the passage.

7. The method of claim 6, wherein expanding at least one of the first end portion and the second end portion comprises allowing self-expansion of at least one of the first end portion and the second end portion.

8. The method of claim 6, wherein expanding at least one of the first end portion and the second end portion comprises balloon expanding at least one of the first end portion and the second end portion.

9. The method of claim 6, wherein the first vessel is an artery and the second vessel is a vein.

10. The method of claim 6, further comprising a polymer material coupled to at least the intermediate portion, wherein the first end portion has a first diameter, wherein the first end portion is substantially cylindrical, wherein the second end portion has a second diameter larger than the first diameter, and wherein the intermediate portion tapers between the first end portion and the second end portion.

11. The method of claim 6, further comprising forming the passage between the first vessel and the second vessel, wherein forming the passage comprises:
      inserting a first catheter in the first vessel upstream of an occlusion site in the first vessel; and
      deploying a needle from the first catheter, through tissue between the first vessel and the second vessel, and into the second vessel, and
   wherein deploying the device in the first vessel, the second vessel, and the passage further comprises:
      inserting a guidewire through the needle;
      retracting the needle and the catheter;
      guiding a delivery catheter carrying the device to the passage using the guidewire; and
      deploying the device from the delivery catheter.

12. A method of forming a channel between a first vessel and a second vessel, the method comprising:
   deploying a device in the first vessel, the second vessel, and a passage between the first vessel and the second vessel, the device comprising:
      a first end portion having a first radial stiffness;

a second end portion having a second radial stiffness; and an intermediate portion longitudinally between the first end portion and the second end portion, the intermediate portion having a third radial stiffness less than the first radial stiffness and the second radial stiffness;

wherein deploying the device in the first vessel, the second vessel, and the passage comprises:

expanding the first end portion against sidewalls of the first vessel;

expanding the second end portion against sidewalls of the second vessel; and expanding the intermediate portion in the passage.

13. The method of claim 12, wherein the first vessel is an artery and the second vessel is a vein.

14. The method of claim 12, comprising dilating the passage.

15. The method of claim 12, wherein expanding the first end portion and the second end portion comprises allowing self-expansion of at least one of the first end portion and the second end portion.

16. The method of claim 12, wherein expanding the first end portion and the second end portion comprises balloon expanding at least one of the first end portion and the second end portion.

17. The method of claim 12, further comprising forming the passage, wherein forming the passage comprises deploying a needle between the first vessel and the second vessel.

18. The method of claim 17, wherein deploying the device in the first vessel, the second vessel, and the passage further comprises:

inserting a guidewire through the needle;

retracting the needle;

guiding a delivery catheter carrying the device to the passage using the guidewire; and deploying the device from the delivery catheter.

19. The method of claim 12, further comprising a polymer material coupled to at least the intermediate portion, wherein the first end portion has a first diameter, wherein the first end portion is substantially cylindrical, wherein the second end portion has a second diameter larger than the first diameter, and wherein the intermediate portion tapers between the first end portion and the second end portion.

20. The method of claim 19, wherein the second end portion tapers between the intermediate portion and the second diameter.

* * * * *